US008039589B1

(12) United States Patent
Chen

(10) Patent No.: US 8,039,589 B1
(45) Date of Patent: Oct. 18, 2011

(54) B7-DC VARIANTS

(75) Inventor: Lieping Chen, Sparks Glencoe, MD (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 309 days.

(21) Appl. No.: 11/932,471

(22) Filed: Oct. 31, 2007

Related U.S. Application Data

(62) Division of application No. 10/679,775, filed on Oct. 6, 2003, now Pat. No. 7,432,351.

(60) Provisional application No. 60/416,203, filed on Oct. 4, 2002.

(51) Int. Cl.
*C07K 14/00* (2006.01)
(52) U.S. Cl. ...................................................... 530/350
(58) Field of Classification Search ........................ None
See application file for complete search history.

(56) References Cited

U.S. PATENT DOCUMENTS

| | | | |
|---|---|---|---|
| 4,272,398 A | 6/1981 | Jaffe |
| 4,376,110 A | 3/1983 | David et al. |
| 4,650,764 A | 3/1987 | Temin et al. |
| 4,769,330 A | 9/1988 | Paoletti et al. |
| 4,861,627 A | 8/1989 | Mathiowitz et al. |
| 4,861,719 A | 8/1989 | Miller |
| 4,925,673 A | 5/1990 | Steiner et al. |
| 4,980,289 A | 12/1990 | Temin et al. |
| 5,013,556 A | 5/1991 | Woodle et al. |
| 5,124,263 A | 6/1992 | Temin et al. |
| 5,155,020 A | 10/1992 | Paoletti |
| 5,155,027 A | 10/1992 | Sledziewski et al. |
| 5,175,099 A | 12/1992 | Wills |
| 5,204,243 A | 4/1993 | Paoletti |
| 5,225,336 A | 7/1993 | Paoletti |
| 5,225,538 A | 7/1993 | Capon et al. |
| 5,240,846 A | 8/1993 | Collins et al. |
| 5,278,056 A | 1/1994 | Bank et al. |
| 5,284,656 A | 2/1994 | Platz et al. |
| 5,451,569 A | 9/1995 | Wong et al. |
| 5,521,288 A | 5/1996 | Linsley et al. |
| 5,567,584 A | 10/1996 | Sledziewski et al. |
| 5,675,848 A | 10/1997 | Kappel |
| 5,714,147 A | 2/1998 | Capon et al. |
| 5,750,375 A | 5/1998 | Sledziewski et al. |
| 5,843,725 A | 12/1998 | Sledziewski et al. |
| 5,861,310 A | 1/1999 | Freeman et al. |
| 5,942,607 A | 8/1999 | Freeman et al. |
| 6,018,026 A | 1/2000 | Sledziewski et al. |
| 6,291,212 B1 | 9/2001 | Sledziewski et al. |
| 6,291,646 B1 | 9/2001 | Sledziewski et al. |
| 6,300,099 B1 | 10/2001 | Sledziewski et al. |
| 6,323,323 B1 | 11/2001 | Sledziewski et al. |
| 6,630,575 B2 | 10/2003 | Coyle et al. |
| 6,635,750 B1 | 10/2003 | Coyle et al. |
| 6,743,619 B1 | 6/2004 | Tang et al. |
| 6,919,193 B2 | 7/2005 | Tang et al. |
| 6,965,018 B2 | 11/2005 | Mikesell et al. |
| 7,029,674 B2 | 4/2006 | Carreno et al. |
| 7,030,219 B2 | 4/2006 | Pardol et al. |
| 7,122,351 B2 | 10/2006 | Moore et al. |
| 7,279,567 B2 | 10/2007 | Mikesell et al. |
| 7,358,354 B2 | 4/2008 | Mikesell et al. |
| 7,368,531 B2 | 5/2008 | Rosen et al. |
| 7,381,794 B2 | 6/2008 | Moore et al. |
| 7,414,122 B2 | 8/2008 | Fox et al. |
| 7,432,059 B2 | 10/2008 | Freeman et al. |
| 7,432,062 B2 | 10/2008 | Coyle et al. |
| 7,432,351 B1 | 10/2008 | Chen |
| 7,560,540 B2 | 7/2009 | Pardoll et al. |
| 7,563,869 B2 | 7/2009 | Honjo et al. |
| 7,595,048 B2 | 9/2009 | Honjo et al. |
| 7,709,214 B2 | 5/2010 | Freeman et al. |
| 7,723,479 B2 | 5/2010 | Mikesell et al. |
| 2002/0091246 A1* | 7/2002 | Pardoll et al. ............... 536/23.2 |
| 2002/0095024 A1 | 7/2002 | Mikesell et al. |
| 2002/0106730 A1 | 8/2002 | Coyle et al. |
| 2002/0107363 A1 | 8/2002 | Fox et al. |
| 2002/0110836 A1 | 8/2002 | Freeman et al. |
| 2002/0164600 A1 | 11/2002 | Freeman et al. |
| 2003/0142359 A1 | 7/2003 | Bean et al. |
| 2003/0171551 A1 | 9/2003 | Rosenblatt et al. |
| 2003/0208058 A1 | 11/2003 | Fiscella et al. |
| 2003/0232323 A1 | 12/2003 | Freeman et al. |
| 2004/0010134 A1 | 1/2004 | Rosen et al. |
| 2005/0228170 A1 | 10/2005 | Fox et al. |
| 2005/0260716 A1 | 11/2005 | Moore et al. |
| 2006/0034826 A1 | 2/2006 | Carreno et al. |
| 2006/0084794 A1 | 4/2006 | Rosen et al. |
| 2006/0110383 A1 | 5/2006 | Honjo et al. |

(Continued)

FOREIGN PATENT DOCUMENTS

EP 1 074 617 2/2001

(Continued)

OTHER PUBLICATIONS

Agata et al., "Expression of the PD-1 antigen on the surface of stimulated mouse T and B lymphocytes," *International Immunology*, 1996, 8:765-772.
Bajorath et al., "Molecular modeling of CD28 and three-dimensional analysis of residue conservation in the CD28/CD152 family," *J. Mol. Graph. Model.*, 1997, 15:135-139.
Berman et al., "The Protein Data Bank," *Nucl. Acids Res.*, 2000, 28:235-242.
Chambers and Allison, "Co-stimulation in T cell responses," *Curr. Opin. Immunol.*, 1997, 9:396-404.
Chapoval et al., "B7-H3: A costimulatory molecule for T cell activation and IFN-γ production," *Nature Immunology*, 2001, 2:269-274.
Connolly, "Analytical Molecular Surface Calculation," *J. Appl. Cryst.*, 1983, 16:548-558.

(Continued)

*Primary Examiner* — Ilia Ouspenski

(74) *Attorney, Agent, or Firm* — Fish & Richardson P.C.

(57) ABSTRACT

Variant costimulatory polypeptides, nucleic acids encoding such polypeptides, and methods for using the polypeptides and nucleic acids to enhance a T cell response are provided herein.

57 Claims, 12 Drawing Sheets

U.S. PATENT DOCUMENTS

| | | |
|---|---|---|
| 2006/0223088 A1 | 10/2006 | Rosen et al. |
| 2007/0037206 A1 | 2/2007 | Rosen et al. |
| 2007/0041963 A1 | 2/2007 | Rosen et al. |
| 2007/0065427 A1 | 3/2007 | Freeman et al. |
| 2007/0092504 A1 | 4/2007 | Carreno et al. |
| 2007/0099833 A1 | 5/2007 | Rosen et al. |
| 2007/0122378 A1 | 5/2007 | Freeman et al. |
| 2007/0224663 A1 | 9/2007 | Rosen et al. |
| 2008/0025979 A1 | 1/2008 | Honjo et al. |
| 2008/0118511 A1 | 5/2008 | Freeman et al. |
| 2008/0226662 A1 | 9/2008 | Pardoll et al. |
| 2008/0241175 A1 | 10/2008 | Pardoll et al. |
| 2009/0042292 A1* | 2/2009 | Chen .......................... 435/375 |
| 2009/0075338 A1 | 3/2009 | Moore et al. |
| 2009/0269783 A1 | 10/2009 | Coyle et al. |

FOREIGN PATENT DOCUMENTS

| | | |
|---|---|---|
| WO | 90/07861 | 7/1990 |
| WO | 91/10741 | 7/1991 |
| WO | 91/17271 | 11/1991 |
| WO | 92/00092 | 1/1992 |
| WO | 92/01047 | 1/1992 |
| WO | 92/20791 | 11/1992 |
| WO | 93/01222 | 1/1993 |
| WO | 95/05464 | 2/1995 |
| WO | 95/07707 | 3/1995 |
| WO | 97/17613 | 5/1997 |
| WO | 97/17614 | 5/1997 |
| WO | 97/24447 | 7/1997 |
| WO | 98/23635 | 6/1998 |
| WO | 98/33914 | 8/1998 |
| WO | 99/64597 | 12/1999 |
| WO | 00/55375 | 9/2000 |
| WO | 00/61612 | 10/2000 |
| WO | 01/34629 | 5/2001 |
| WO | 01/70979 | 9/2001 |
| WO | 01/83750 | 11/2001 |
| WO | 01/94413 | 12/2001 |
| WO | 02/00692 | 1/2002 |
| WO | 02/00730 | 1/2002 |
| WO | 02/02587 | 1/2002 |
| WO | 02/02891 | 1/2002 |
| WO | 02/08279 | 1/2002 |
| WO | 02/78731 | 1/2002 |
| WO | 02/24891 | 3/2002 |
| WO | 02/057453 | 7/2002 |
| WO | 02/079474 | 10/2002 |
| WO | 02/081731 | 10/2002 |
| WO | 03/008583 | 1/2003 |
| WO | 2006/050172 | 5/2006 |
| WO | 2008/037080 | 4/2008 |
| WO | 2009/114110 | 9/2009 |
| WO | 2010/027423 | 3/2010 |
| WO | 2010/027827 | 3/2010 |
| WO | 2010/027828 | 3/2010 |
| WO | 2010/098788 | 9/2010 |

OTHER PUBLICATIONS

Cristiano and Roth, "Molecular conjugates: a targeted gene delivery vector for molecular medicine," *J. Mol. Med.*, 1995, 73:479-486.

Dong et al., "Tumor-associated B7-H1 promotes T-cell apoptosis: A potential mechanism of immune evasion," *Nature Medicine*, 2002, 8:793-800.

Dong et al., "B7-H1, a third member of the B7 family, co-stimulates T-cell proliferation and interleukin-10 secretion," *Nature Med.*, 1999, 5:1365-1369.

Engh and Huber, "Accurate Bond and Angle Parameters for X-Ray Protein Structure Refinement," *Acta Cryst.*, 1991, A47:392-400.

Fechteler et al., "Prediction of Protein Three-dimensional Structures in Insertion and Deletion Regions: A Procedure for Searching Data Bases of Representative Protein Fragments Using Geometric Scoring Criteria," *J. Mol. Biol.*, 1995, 253:114-131.

Freeman et al., "Engagement of the PD-1 Immunoinhibitory Receptor by a Novel B7 Family Member Leads to Negative Regulation of Lymphocyte Activation," *J. Exp. Med.*, 192:1027-1034.

Guatelli et al., "Isothermal, in vitro amplification of nucleic acids by a multienzyme reaction modeled after retroviral replication," *Proc. Natl. Acad. Sci. USA*, 1990, 87:1874-1878.

Hyrup et al., "Peptide Nucleic Acids (PNA): Synthesis, Properties and Potential Applications," *Bioorgan. Med. Chem.*, 1996, 4:5-23.

Ikemizu et al., "Structure and Dimerization of a Soluble Form of B7-1," *Immunity*, 2000, 12:51-60.

Ishida et al., "Induced expression of PD-1, a novel member of the immunoglobulin gene superfamily, upon programmed cell death," *EMBO J.*, 1992, 11:3887-3895.

Ishida et al., "Differential expression of PD-L1 and PD-L2, ligands for an inhibitory receptor PD-1, in the cells of lymphohematopoietic tissues," *Immunology Letters*, 2002, 84:57-62.

Krummel and Allison, "CTLA-4 Engagement Inhbits IL-2 Accumulation and Cell Cycle Progression upon Activation of Resting T Cells," *J. Exp. Med.*, 1996, 183:2533-2540.

Latchman et al., "PD-L2 is a second ligand for PD-1 and inhibits T cell activation," *Nature Immunology*, 2001, 2:261-268.

Lenschow et al., "CD28/B7 System of 258 T Cell Costimulation," *Annu. Rev. Immunol.*, 1996, 14:233-258.

Levitt, "Accurate Modeling of Protein Conformation by Automatic Segment Matching," *J. Mol. Biol.*, 1992, 226:507-533.

Lewis, "PCR's Competitors Are Alive and Well and Moving Rapidly Towards Commercialization," *Genetic Engineering News*, 1992, vol. 12, 3 pages.

Nishimura et al., "Development of Lupus-like Autoimmune Diseases by Disruption of the *PD-1* Gene Encoding an ITIM Motif-Carrying Immunoreceptor," *Immunity*, 1999, 11:141-151.

Nishimura et al., "Immunological studies on PD-1-deficient mice: implication of PD-1 as a negative regulator for B cell responses," *International Immunology*, 1998, 10:1563-1572.

Nishimura et al., "Autoimmune Dilated Cardiomyopathy in PD-1 Receptor-Deficient Mice," *Science*, 2001, 291:319-322.

Ostrov et al., "Structure of Murine CTLA-4 and Its Role in Modulating T Cell Responsiveness," *Science*, 2000, 290:816-819.

Penix et al., "Two Essential Regulatory Elements in the Human Interferon γ Promoter Confer Activation Specific Expression in T Cells," *J. Exp. Med.*, 1993, 178:1483-1496.

Ponder et al., "Tertiary Templates for Proteins—Use of Packing Criteria in the Enumeration of Allowed Sequences for Different Structural Classes," *J. Mol. Biol.*, 1987, 193:775-791.

Rathmell and Thompson, "The Central Effectors of Cell Death in the Immune System," *Annu. Rev. Immunol.*, 1999, 17:781-828.

Schwartz et al., "Structural mechanisms of costimulation," *Nature Immunology*, 2002, 3:427-434.

Schwartz et al., "Structural basis for co-stimulation by the human CTLA4/B7-2 complex," *Nature*, 2001, 410:604-608.

Stamper et al., "Crystal structure of the B7-1/CTLA-4 complex that inhibits human immune responses," *Nature*, 2001, 410:608-611.

Summerton and Weller, "Morpholino Antisense Oligomers: Design, Preparation and Properties," *Antisense Nucleic Acid Drug Dev.*, 1997, 7:187-195.

Swallow et al., "B7h, a Novel Costimulatory Homolog of B7.1 and B7.2, Is Induced by TNFα," *Immunity*, 1999, 1:423-432.

Tamura et al., "B7-H1 costimulation preferentially enhances CD28-indepenent T-helper cell function," *Blood*, 2001, 97:1809-1816.

Thompson et al., "*cis*-Acting Sequences Required for Inducible Interleukin-2 Enhancer Function Bind a Novel Ets-Related Protein, Elf-1," *Mol. Cell. Biol.*, 1992, 12:1043-1053.

Todd et al., "Transcription of the Interleukin 4 Gene Is Regulated by Multiple Promoter Elements," *J. Exp. Med.*, 1993, 177:1663-1674.

Tseng et al., "B7-DC, a New Dendritic Cell Molecule with Potent Costimulatory Properties for T Cells," *J. Exp. Med.*, 2001, 193:839-845.

Walunas et al., "CTLA-4 Ligation Blocks CD28-dependent T Cell Activation," *J. Exp. Med.*, 1996, 183:2541-2550.

Wang et al., "Ligand Binding Sites of Inducible Costimulator and High Avidity Mutants with Improved Function," *J. Exp. Med.*, 2002, 195:1033-1041.

Wang et al., "Costimulation of T cells by B7-H2, a B7-like molecule that binds ICOS," *Blood*, 2000, 96:2808-2813.

Weiss, "Hot Prospect for New Gene Amplifier: Ligase chain reaction, a combination DNA amplifier and genetic screen could do for DNA diagnostics what PCR has done for basic molecular biology," *Science*, 1991, 254:1292-1293.

Williams and Barclay, "The Immunoglobulin Superfamily—Domains for Cell Surface Recognition," *Ann. Rev. Immunol.*, 1988, 6:381-405.

Wong et al., "Human GM-CSF: Molecular Cloning of the Complementary DNA and Purification of the Natural and Recombinant Proteins," *Science*, 1985, 228:810-815.

Yoshinaga et al., "T-cell co-stimulation through B7RP-1 and ICOS," *Nature*, 1999, 402:827-832.

U.S. Appl. No. 11/932,471, filed Oct. 31, 2007, Chen.

ACSADI et al., "Direct gene transfer and expression into rat heart in vivo", *The New Biologist*, 3:71-81 (1991).

Aldovini, "Humoral and cell-mediated immune responses to live recombinant BCG-HIV vaccines," *Nature*, 351: 479-482 (1991).

Anderson, "Human gene therapy", *Science*, 256:808-813 (1992).

Attwood et al., Genomics. The babel of bioinformatics, *Science*, 290(5491):471-3 (2000).

Benita et al., "Characterization of drug-loaded poly(d,l-lactide) microspheres", *J. Pharm. Sci.*, 73:1721-1724 (1984).

Bona and Hiernaux et al., "Immune respone: Idiotype anti-idiotype network", *CRC Crit. Rev. Immunol.*, 33-81 (1981).

Bonifaz et al., "Efficient targeting of protein antigen to the dendritic cell receptor DEC-205 in the steady state leads to antigen presentation on major histocompatibility complex class I products and peripheral CD8+ T cell tolerance", *J. Exp. Med*, 196(12):1627-38 (2002).

Bonifaz et al., "In vivo targeting of antigens to maturing dendritic cells via the DEC-205 receptor improves T cell vaccination", *J. Exp. Med*, 199(6):815-24 (2004).

Braquet et al., "Effect of Endothelin-1 on Blood Pressure and Bronchopulmonary System of the Guinea Pig", *J. Cardiovascular Pharmacology*, 13(85):SI43-S146 (1989).

Chakrabarti et al., "Vaccinia virus expression vector: coexpression of beta-galactosidase provides visual screening of recombinant virus plaques", *Mol. and Cell. Biol.*, 5:3403-3409 (1985).

Chen, "Co-inhibitory molecules of the B7-CD28 family in the control of T-cell immunity", *Nat Rev. Immunol.*, 4(5):336-47 (2004).

Chen et al., "Constimulation of antitumor immunity by the B7 counterreceptor of the T lymphocyte molecules CD28 and CTLA-4", *Cell*, 71:1093-1102 (1992).

Choi et al., "Genomic organization and expression analysis of B7-H4, an immune inhibitory molecule of the B7 family", *J. Immunol*, 171:4650-4654 (2003).

Cone et al., "High-efficiency gene transfer into mammalian cells: generation of helper-free recombinant retrovirus with broad mammalian host range", *Proc. Natl. Acad. Sci. USA*, 81:6349-6353 (1984).

Coyle et al., "The expanding B7 superfamily: increasing complexity in costimulatory signals regulating T cell function", *Nature Immunol.*, 2(3): 203-9 (2001).

Crystal, "Gene therapy strategies for pulmonary disease" *Amer. J. Med.*, 92(suppl6A):44S-52S (1992).

Database EM-HUM [Online] EMBL; Accession No: AK001872 (Feb. 22, 2000).

Database EM-MUS [Online]EMBL; Accession No: AF142780.1 (version 1), Jun. 1, 1999).

Debs et al., "Lung-specific delivery of cytokines induces sustained pulmonary and systemic immunomodulation in rats", *J Immunol.*, 140:3482-3488 (1988).

Dong et al., "Immune regulation by novel costimulatory molecules", *Immunol. Res.*, 28(1):39-48 (2003).

Dudler et al., "Gene transfer of programmed death Ligand-1.1g prolongs cardiac allograft survival", *Transplantation*, 82(12):1733-7 (2006).

Dunussi-Joannopoulos et al., "Gene Therapy with B7.1 and GM-CSF Vaccines in a Murine AML Model", *J. Pediatr. Hematol. Oncol.*, 19(6):536-540 (1997).

EMBL-EBI Accession No. AF 142780.2 (version 2, accessed Sep. 28, 2009), (Jun. 1, 1999).

EMBL-EBI Accession No. Q9WUL5 (Nov. 1, 1999).

European Examination Report for Bristol-Myers Squibb Co., App. No. 07 023 993.4-1521, Dated May 19, 2010.

Falkner et al., "pUV I: a new vaccinia virus insertion and expression vector", *Nucl. Acids Res*, 15:7192 (1987).

Freeman et al., "B7, a new member of the Ig superfamily with unique expression on activated and neoplastic B cells", *The Journal of Immunology*, 143 (8); 2714-2722 (1989).

Freeman et al., "Structure, expression, and T cell proliferation costimulatory activity of the murine homologue of the human Blymphocyte activation antigen B7", *J. Exp. Med.*, 174:625-631 (1991).

Freeman et al., "Cloning of B7-2: a CTLA-4 counter-receptor that costimulates human T cell proliferation", *Science*, 262:909-911 (1993).

Fuerst et al, "Transfer of the inducible *lac* repressor/operator system from *Escherichia coli* to a vaccinia expression vector", *Proc. Natl. Acad. Sci. USA*, 86:2549-2553 (1989).

GenBank Accession No. AK001872.1,"*Homo sapiens* cDNA FLJ11010 fis, clone PLACE1003145", pp. 1-2, (submitted Feb. 16, 2000).

GenBank Accession No. AL162253, "Human DNA sequence from clone RP11-574F11 on chromosome 9 contains the gene for B7-H1 protein (PD-L1), the gene for programmed death ligan 2 (PDL2) (PDCD1L2) and a novel gene", pp. 1-36 (Mar. 24, 2000).

Gerstmayer et al., "Costimulation of T-cell proliferation by a chimeric B7 antibody fusion protein", *Cancer Immunology Immunotherapy*, 45(3-4): 156-158 (1997).

Gerstmayer et al., "Costimulation of T cell proliferation by a chimeric B7-2 antibody fusion protein specifically targeted to cells expressin the *erb*B2 proto-oncogene," *J. Immunol*, 158 (10): 4584-90 (1997).

Gimmi et al, "B-cell surface antigen B7 provides a costimulatory signal that induces T cells to proliferate and secrete interleukin 2", *Proc. Natl. Acad. Sci*, 88:6576-6570 (1991).

Goodwin et al., "Molecular Cloning and Expression of the Type 1 and Type 2 Murine Receptors for the Tumor Necrosis Factor", *Mol. and Cell. Biol.*, 11(6): 3020-3026 (1991).

Greenwald et al., "The B7 family revisited", *Annu. Rev. Immunol.*, 23: 515-48 (2005).

Guo et al., "A novel fusion protein of IP10-scFv retains antibody specificity and chemokine function," *Biochem. Biophys. Res. Commun.*, 320(2):506-13 (2004).

Hatzoglou et el., "Hepatic gene transfer in animals using retroviruses containing the promoter from the gene for phosphoenolpyruvate carboxykinase" *J. Biol. Chem.*, 265:17285-93 (1990).

Hawiger et el., "Dendritic cells induce peripheral T cell unresponsiveness under steady state conditions in vivo", *Exp. Med.*, 194(6):769-79 (2001).

Henry et el., "Cloning, structural analysis, and mapping of the B30 and B7 multigen families to the major histocompatibility complex (MHC) and other chromosomal regions", *Immunogenetics*, 56:385-395 (1997).

Henry et el., "Structure and evolution of the extended B7 family", *Immunology Today*, 20(6):285-288 (1999).

Hentikoff and Hentikoff, "Amino acid substitution matrices from protein block", *Pros. Natl. Acad. Sci. U.S.A.*, 89:10915-10919 (1992).

Hiroishi et al., "Interferon-alpha gene therapy in combination with CDS0 transduction reduces tumorigenicity and growth of established tumor in poorly immunogenic tumor models", *Gene Ther.*, 6:1988-1994 (1999).

Hochman et al., "An active antibody fragment (Fv) composed of the variable portions of heavy and light chains", *Biochemistry*, 12:1130-1135 (1973).

Hock et al., "Retrovirus-mediated transfer and expression of drug resistance genes in human haematopoietic progenitor cells", *Nature*, 320:275-77 (1986).

Hoiseth and Stocker, Aromatic-dependent *Salmonella typhimurium* are non-virulent and effective as live vaccines, *Nature*, 291, 238-239 (1981).

Hubbard et al., "Anti-neutrophil-elastase defenses of the lower respiratory tract in alpha 1-antitrypsin deficiency directly augmented with an aerosol of alpha 1-antitrypsin", *Annals of Internal Medicine*, 3:206-Z12 (1989).

Ikonomidis, "Delivery of a viral antigen to the class I processing and presentation pathway by Listeria monocytogenes," *J. Exp. Med.*, 180:2209-2218 (1994).

Linsley et al., "T-cell antigen C028 mediates adhesion with B cells by interacting with activation antigen 87188-1," *Proc. Nat, Acad. Sci.*, 87:5031-5035 (1990).

Jerne, "Towards a network theory of the immune system", *Ann. Immunol*, 125C:373-389 (1974).

Johnston et al., "Biolistic Transformation (1991) of Animal Tissue", *In Vitro Cell Dev. Biol.*, 27P:11-14 (1991).

Kaleko et al., "Persistent gene expression after retroviral gene transfer into liver cells in vivo," *Human Gene Therapy*, 2:27-32, 1991.

Kaufman et al., "A phase I trial of intra lesional RV-B7.1 vaccine in the treatment of malignant melanoma," *Hum. Gene. Ther.*, 2000, 11: 1065-1082.

Koehler and Milstein, "Continuous cultures of fused cells secreting antibody of predefined specificity," *Nature*, 256: 495-497 (1975).

Kohn et al. "Gene therapy for genetic diseases", *Cancer Invest.*, 7:179-192 (1989).

Kuiper et al., "B7.1 and cytokines: Synergy in cancer gene therapy", *Avd. Ex. Med. Biol.* 465:381-390 (2000).

Lenshow et al., "CD28/B7 System of 258 T Cell Costimulation," *Annu. Rev. Immunol.*, 1996, 14:233-258.

Lewinski, et al., Retroviral DNA integration: viral and cellular determinants of target-site selection, *PLoS Pathog.*, 2(6): e60 (2006).

Linsley et al., "Binding of the B cells activation antigen B7 to C028 costimulates T cell proliferation and interleukin 2 mRNA accumulation", *J. Exp. Med.*, 173:721-730 (1991).

Linsley et al., Extending the B7 (CD80) gene family, *Protein Sci.*, 3(8): 1341-1343 (1994).

Liu et al., B7DC/PDL2 promotes tumor immunity by a PD-1-independent mechanism, *J. Exp. Med.*, 197(12): 1721-30 (2003).

Lu et el., "EGF-IL-18 fusion protein as a potential anti-tumor reagent by induction of immune response and apoptosis in cancer cells," *CancerLett.*, 60(1-2):187-97 (2008).

Mann et al., "Construction of a retrovirus packaging mutant and its use to produce helper-free defective retrovirus" *Cell*, 33:153-159 (1983).

Martin et al. "Combination gene therapy with CD86 and the MHC Class II transactivator in the control of lung tumor growth", *J. Immunol.*, 162:6663-6670 (1999).

Mathiowitz et al., "Morphology of polyanhydride microsphere delivery systems",*Scanning Microscopy*, 4: 329-340 (1990).

Mathiowitz and Langer, "Polyanhydride microspheres as drug carriers. I. Hot-melt microencapsulation", *J. Controlled Release*, 5:13-22 (1987).

Mathiowitz, Novel microcapsules for delivery systems , *Reactive Polymers*, 6:275-283 (1987).

Mathiowitz, "Polyanhydride microspheres as drug carriers, II. microencapsulation by solvent removal", *J. Appl. Polymer Sci.*, 35: 755-774 (1988).

Mathiowitz et al., "Polyanhydride microspheres. IV. Morphology and characterization of systems made by spray drying", *J. Appl. Polymer Sci.*, 45: 125-134 (1992).

McLachlin et al., "Retroviral-mediated gene transfer", *Prog. Nuc. Acid Res. Molec. Biol.*, 38: 91-135, 1990.

Metzler et al., "Solution structure of human CTLA-4 and delineation of a CD80/CD86 binding site conserved in CD28", *Nature Structural Biol.*, 4(7):527-531 (1997).

Miller et al., "Generation of helper-free amphotropic retroviruses that transduce a dominant-acting, methotrexate-resistant dihydrofolate reductase gene", *Molec. Cell. Biol.*, 5:431-437 (1985).

Miller et al., "Redesign of retrovirus packaging cell lines to avoid recombination leading to helper virus production", *Molec. Cell. Biol.*, 6:2895-2902 (1986).

Miller et al., Gene transfer by retrovirus vectors occurs only in cells that are actively replicating at the time of infection, *Mol. Cell Biol.*, 10:4239 (1990).

Miller, "Human gene therapy comes of age", *Nature*, 357:455-460 (1992).

Moss, "Poxvirus expression vectors", *Curr. Top. Microbiol. Lmmunol.*, 158:25-38 (1992).

Moss, "Poxvirus vectors: cytoplasmic expression of transferred genes", *Curt. Opin. Genet. Dev.*, 3:86-90 (1993).

Moss, "Use of vaccinia virus as a n infectious molecular cloning and expression vector", *Gene Amplif Anal*,3:201-213 (1983).

Moss, "Vaccinia virus vectors", *Biotechnology*, 20:345-362 (1992).

Moss, "Vaccinia virus: a tool for research and vaccine development", *Science* ,252:1662-1667 (1991).

Nabel et al., "Recombinant gene expression in vivo within endothelial cells of the arterial wall", *Science*, 244(4910):1342-4 (1989).

Nechiporuk et al., "The mouse SCA2 gene: cDNA sequence, alternative splicing and protein expression", *Human Mol. Gen.*, 7(8):1301-1309 (1998).

Needleman and Wunsch, "A general method applicable to the Search for similarities in the amino acid sequence of two proteins", *J. Mol. Biol.*, 48:443-453(1970).

Newmark et al., "Preparation and properties of adducts of streptokinase and streptokinase-plasmin complex with polyethylene glycol and pluronic Polyol F38", *J. Appl. Biochem.*, 4:185-189 (1982).

Nicolau et al., "In vivo expression of rat insulin after intravenous administration of the liposome-entrapped gene for rat insulin I", *Proc. Natl. Acad. Sci. USA*, 80:1068-72 (1983).

Oezkaynak, "Programmed death-1 targeting can promote allograft survival", *J. Immunol*, 169(11):6546-53 (2002).

Peach et al., "Both extracellular immunoglobin-Iike domains of CD80 contain residues critical for binding T cell surface receptors CTLA-4 and CD28", *J. Biol. Chem*, 270(36):21181-21187 (1995).

Piccini, "Vaccinia: virus, vector, vaccine", *Adv. Virus Res.*, 34:43-64 (1988).

Plueckthun et al., "Expression of functional antibody Fv and Fab fragments in *Escherichia coli*," *Methods Enzymol.*, 178:497-515 (1989).

Poirier, "Protective immunity evoked by oral administration of attenuated aroA *Salmonella typhimurium* expressing cloned streptococcal M protein", *J. Exp. Med.*, 168:25-32 (1988).

Prasad et al., "B7S1, a novel B7 family member that negatively regulates T cell activation", *Immunity*,18: 863-873 (2003).

Radhakrishnan et al., "Dendritic Cells activated by cross-linking BT-DC (PD-L2) block inflammatory airway disease", *J. Allergy Clin. Immunol*, 116(3):668-74 (2005).

Rajewsky et al., "Genetics, expression, and function of ioiotypes," *Ann. Rev. Immunol.*, 1983, 1:569-607.

Razi-Wolf, "Expression and function of the murine B7 antigen, the major costimulatory molecule expressed by peritoneal exudate cells", *Proc. Nat Acad, Sc.*, 89:4210-4214 (1992).

Renauld et al Expression cloning of the murine and human interleukin 9 receptor cDNAs', *Proc. Natl.Acad. Sci, USA*, 89:5690. 5694 (1992).

Rosenfeld et al., "Adenovirus-mediated transfer of a recombinant alpha 1-antitrypsin gene to the lung epithelium in vivo," *Science*, 1991, 252: 431-433.

Rousseaux et al, "Optimal conditions for the preparation of proteolytic fragments from monoclonal IgG of different rat IgG subclasses," *Meth. Enzymol.*, 1986, 121: 663-669.

Sadoff, "Oral *Salmonella typhimurium* vaccine expressing circumsporozoite protein protects against malaria," *Science*, 1988, 240: 336-338.

Salib et al., "Utilization of sodium alginate in drug microencapsulation," *Pharmazeutische Industrie*, 1978, 40(11A): 1230-1234.

Samulski, "Targeted integration of adenoassociated cirus (AAV) into human chromosome 19," *EMBO J.*, 1991, 10: 3941-3950.

Sanni et al., "Evolution of aminoacyl-tRNA synthetase quaternary structure and activity: *Saccharomyces cerevisiae* mitochondrial phenylalanyl-tRNA synthetase," *Proc. Natl. Acad. Sci. USA*, 1991, 88: 8387-8391.

Sawhney et al., "Bioerodible hydrogels based on photopholymerized poly(ethylene glycol)-co-poly(.alpha.-hydroxy acid) diacrylate macromers," *Macromolecules*, 1993, 26: 581-587.

Schafer, "Induction of a cellular immune response to a foreign antigen by a recombinant *Listeria monocytogenes* vaccine," *J. Immunol.*, 1992, 149: 53-59.

Schwartz et al, "Costimulation of T lymphocytes: the role of CD28, CTLA-4, and B7/BBI in interluekin-2 production and immunotherapy", *Cell*, 71:1065-1068 (1992).

Zelenin et al., "High-velocity mechanical DNA transfer of the chloramphenicolacetyl transferase gene into rodent liver, kidney and mammary gland cells in organ explants and in vivo," *FEBS Lett.*, 1991, 280-94-6.

Sharon et al., "Preparation of Fv fragment from the mouse myeloma XRPC-25 immunoglobulin possessing anti-dinitrophenyl activity," *Biochemistry*, 1976, 15: 1591-1594.

Shin et al., "Cooperative B7-1/2 (CD80/CD86) and B7-DC costimulation of CD4+ T cells independent of the PD-1 receptor", *J. Exp. Med.*, 198(1):31-38 (2003).

Sica et al., "B7-H4, a molecule of the B7 family, negatively regulates T cell immunity," *Immunity*, 2003, 18: 849-861.

Skerra et al., "Assembly of a functional immunoglobulin Fv fragment in *Escherichia coli*," *Science*, 1988, 240: 1038-1041.

Skolnick et al., "From genes to protein structure and function: novel applications of computational approaches in the genomic era", *Trends in Biotechnology*, 18(1):34-39 (2000).

Smith et al., "Pulmonary deposition and clearance of aerosolized alpha-1-proteinase inhibitor administered to dogs and to sheep," *J. Clin. Invest.*, 1989, 84: 1145-1146.

Sorge et al., "Amphotropic retrovirus vector system for human cell gene transfer," *Molec. Cell. Biol.*, 1984, 4: 1730-1737.

Soriano, "Targeted and nontargeted liposomes for in vivo transfer to rat liver cells of a plasmid containing the preproinsulin I gene," *Proc. Natl. Acad. Sci.USA*, 1983, 80: 7128-7131.

Stammers et al "BTL-II: A polymorphic locus with homology to the butyrolphilin gene family, located at the border of the major histocompatibility complex class II and class III regions in human and mouse", *Immunogenetics*, 51(4-5):373-382 (2000).

Sutter et al., "Nonreplicating vaccina vector efficiently expresses recombinant genes," *Proc. Natl. Acad. Sci. USA*, 1992, 89: 10847-10851.

Tazi-Ahnini et al., "Cloning, localization, and structure of new members of the butyrophilin gene family in the juxtatelomenc region of the major histocompatibility complex", *Immunogenetics*, 47:55-63 (1997).

Temin, "Safety considerations in somatic gene therapy of human disease with retrovirus vectors," *Human Gene Therapy*, 1990, 1: 111-23.

Titomirov, "In vivo electroporation and stable transformation of skin cells of newborn mice by plasmid DNA," *Biochem. Biophys. Acta.*, 1991, 1088- 131-134.

Townsend et al., "Tumor rejection after direct costimulation of CD8+ T cells by B7 transfected melanoma cells", *Science*, 259:368-370 (1993).

Wahl et al., "Improved radioimaging and tumor localization with monoclonal F(ab')$_2$," *J. Nuc. Med.*, 1983, 24: 316-325.

Wang, "pH-sensitive immunoliposomes mediate target-cell-specific delivery and controlled expression of a foreign gene in mouse," *Proc. Natl. Acad. Sci*, 1987, 84: 7851.

Williams et al., "Introduction of foreign genes into tissues of living mice by DNA-coated microprojectiles," *Proc. Natl. Proc. Sci. USA*, 1991, 38:2726.

Winter et al., "Man-made antibodies," *Nature*, 1991, 349:293-299.

Wolff, "Direct gene transfer into mouse muscle in vivo," *Science*, 1990, 247: 1465-1468.

Wu, "Receptor-mediated gene delivery and expression in vivo," *J. Biol. Chem.*, 1988, 263: 14621-14624.

Wu, "Targeting genes: delivery and persistent expression of a foreign gene driven by mammalian regulatory elements in vivo," *J. Biol. Chem.*, 1989, 264: 16985-16987.

Yang et al., "In vivo and in vitro gene transfer to mammalian somatic cells by particle bombardment," *Proc. Natl. Acad. Sci. USA*, 1990, 87: 9568-72.

Yang, "Gene transfer into mammalian somatic cells in vivo," *Crit. Rev. Biotechnol.*, 1992, 12: 335-356.

Zang et al., "B7x: a widely expressed by family member that inhibits T cell activation," *Proc. Natl. Acad. Sci. USA*. 2003, 100: 10388-10392.

Zelenin et al., "Genetic transformation of mouse cultured cells with the help of high-velocity mechanical DNA injection," *FEBS Lett.*, 1989, 244: 65-7.

Zwiebel et al., "Drug delivery by genetically engineered cell implants," *Ann. N.Y. Acad. Sci.*, 1991, 618: 694-404.

Winter et al., "Man-made antibodies," *Nature*, 1991, 349:293-299.

\* cited by examiner

Figure 1

MetArgIlePheAlaValPheIlePheMetThrTyrTrpHisLeuLeuAsnAlaPheThrVal

ThrValProLysAspLeuTyrValValGluTyrGlySerAsnMetThrIleGluCysLysPhe

ProValGluLysGlnLeuAspLeuAlaAlaLeuIleValTyrTrpGluMetGluAspLysAsn

IleIleGlnPheValHisGlyGluGluAspLeuLysValGlnHisSerSerTyrArgGlnArg

AlaArgLeuLeuLysAspGlnLeuSerLeuGlyAsnAlaAlaLeuGlnIleThrAspValLys

LeuGlnAspAlaGlyValTyrArgCysMetIleSerTyrGlyGlyAlaAspTyrLysArgIle

ThrValLysValAsnAlaProTyrAsnLysIleAsnGlnArgIleLeuValValAspProVal

ThrSerGluHisGluLeuThrCysGlnAlaGluGlyTyrProLysAlaGluValIleTrpThr

SerSerAspHisGlnValLeuSerGlyLysThrThrThrThrAsnSerLysArgGluGluLys

LeuPheAsnValThrSerThrLeuArgIleAsnThrThrThrAsnGluIlePheTyrCysThr

PheArgArgLeuAspProGluGluAsnHisThrAlaGluLeuValIleProGluLeuProLeu

AlaHisProProAsnGluArgThrHisLeuValIleLeuGlyAlaIleLeuLeuCysLeuGly

ValAlaLeuThrPheIlePheArgLeuArgLysGlyArgMetMetAspValLysLysCysGly

IleGlnAspThrAsnSerLysLysGlnSerAspThrHisLeuGluGluThr (SEQ ID NO:3)

Figure 2

MetArgIlePheAlaGlyIleIlePheThrAlaCysCysHisLeuLeuArgAlaPheThrIle
ThrAlaProLysAspLeuTyrValValGluTyrGlySerAsnValThrMetGluCysArgPhe
ProValGluArgGluLeuAspLeuLeuAlaLeuValValTyrTrpGluLysGluAspGluGln
ValIleGlnPheValAlaGlyGluGluAspLeuLysProGlnHisSerAsnPheArgGlyArg
AlaSerLeuProLysAspGlnLeuLeuLysGlyAsnAlaAlaLeuGlnIleThrAspValLys
LeuGlnAspAlaGlyValTyrCysCysIleIleSerTyrGlyGlyAlaAspTyrLysArgIle
ThrLeuLysValAsnAlaProTyrArgLysIleAsnGlnArgIleSerValAspProAlaThr
SerGluHisGluLeuIleCysGlnAlaGluGlyTyrProGluAlaGluValIleTrpThrAsn
SerAspHisGlnProValSerGlyLysArgSerValThrThrSerArgThrGluGlyMetLeu
LeuAsnValThrSerSerLeuArgValAsnAlaThrAlaAsnAspValPheTyrCysThrPhe
TrpArgSerGlnProGlyGlnAsnHisThrAlaGluLeuIleIleProGluLeuProAlaThr
HisProProGlnAsnArgThrHisTrpValLeuLeuGlySerIleLeuLeuPheLeuIleVal
ValSerThrValLeuLeuPheLeuArgLysGlnValArgMetLeuAspValGluLysCysGly
ValGluAspThrSerSerLysAsnArgAsnAspThrGlnPheGluGluThr (SEQ ID NO:4)

Figure 3

MetIlePheLeuLeuLeuMetLeuSerLeuGluLeuGlnLeuHisGlnIleAlaAla
LeuPheThrValThrValProLysGluLeuTyrIleIleGluHisGlySerAsnVal
ThrLeuGluCysAsnPheAspThrGlySerHisValAsnLeuGlyAlaIleThrAla
SerLeuGlnLysValGluAsnAspThrSerProHisArgGluArgAlaThrLeuLeu
GluGluGlnLeuProLeuGlyLysAlaSerPheHisIleProGlnValGlnValArg
AspGluGlyGlnTyrGlnCysIleIleIleTyrGlyValAlaTrpAspTyrLysTyr
LeuThrLeuLysValLysAlaSerTyrArgLysIleAsnThrHisIleLeuLysVal
ProGluThrAspGluValGluLeuThrCysGlnAlaThrGlyTyrProLeuAlaGlu
ValSerTrpProAsnValSerValProAlaAsnThrSerHisSerArgThrProGlu
GlyLeuTyrGlnValThrSerValLeuArgLeuLysProProProGlyArgAsnPhe
SerCysValPheTrpAsnThrHisValArgGluLeuThrLeuAlaSerIleAspLeu
GlnSerGlnMetGluProArgThrHisProThrTrpLeuLeuHisIlePheIlePro
SerCysIleIleAlaPheIlePheIleAlaThrValIleAlaLeuArgLysGlnLeu
CysGlnLysLeuTyrSerSerLysAspThrThrLysArgProValThrThrThrLys
ArgGluValAsnSerAlaIle (SEQ ID NO:5)

Figure 4

MetLeuLeuLeuLeuProIleLeuAsnLeuSerLeuGlnLeuHisProValAlaAla
LeuPheThrValThrAlaProLysGluValTyrThrValAspValGlySerSerVal
SerLeuGluCysAspPheAspArgArgGluCysThrGluLeuGluGlyIleArgAla
SerLeuGlnLysValGluAsnAspThrSerLeuGlnSerGluArgAlaThrLeuLeu
GluGluGlnLeuProLeuGlyLysAlaLeuPheHisIleProSerValGlnValArg
AspSerGlyGlnTyrArgCysLeuValIleCysGlyAlaAlaTrpAspTyrLysTyr
LeuThrValLysValLysAlaSerTyrMetArgIleAspThrArgIleLeuGluVal
ProGlyThrGlyGluValGlnLeuThrCysGlnAlaArgGlyTyrProLeuAlaGlu
ValSerTrpGlnAsnValSerValProAlaAsnThrSerHisIleArgThrProGlu
GlyLeuTyrGlnValThrSerValLeuArgLeuLysProGlnProSerArgAsnPhe
SerCysMetPheTrpAsnAlaHisMetLysGluLeuThrSerAlaIleIleAspPro
LeuSerArgMetGluProLysValProArgThrTrpProLeuHisValPheIlePro
AlaCysThrIleAlaLeuIlePheLeuAlaIleValIleIleGlnArgLysArgIle (SEQ ID NO:6)

Figure 5

```
atgaggatat ttgctgtctt tatattcatg acctactggc atttgctgaa
cgcatttact gtcacggttc ccaaggacct atatgtggta gagtatggta
gcaatatgac aattgaatgc aaattcccag tagaaaaaca attagacctg
gctgcactaa ttgtctattg ggaaatggag gataagaaca ttattcaatt
tgtgcatgga gaggaagacc tgaaggttca gcatagtagc tacagacaga
gggcccggct gttgaaggac cagctctccc tgggaaatgc tgcacttcag
atcacagatg tgaaattgca ggatgcaggg gtgtaccgct gcatgatcag
ctatggtggt gccgactaca agcgaattac tgtgaaagtc aatgccccat
acaacaaaat caaccaaaga attttggttg tggatccagt cacctctgaa
catgaactga catgtcaggc tgagggctac cccaaggccg aagtcatctg
gacaagcagt gaccatcaag tcctgagtgg taagaccacc accaccaatt
ccaagagaga ggagaagctt ttcaatgtga ccagcacact gagaatcaac
acaacaacta atgagatttt ctactgcact tttaggagat tagatcctga
ggaaaaccat acagctgaat tggtcatccc agaactacct ctggcacatc
ctccaaatga aaggactcac ttggtaattc tgggagccat cttattatgc
cttggtgtag cactgacatt catcttccgt ttaagaaaag ggagaatgat
ggatgtgaaa aaatgtggca tccaagatac aaactcaaag aagcaaagtg
atacacattt ggaggagacg taa
```

(SEQ ID NO:7)

Figure 6

```
atgaggatat ttgctggcat tatattcaca gcctgctgtc acttgctacg
ggcgtttact atcacggctc caaaggactt gtacgtggtg gagtatggca
gcaacgtcac gatggagtgc agattccctg tagaacggga gctggacctg
cttgcgttag tggtgtactg ggaaaaggaa gatgagcaag tgattcagtt
tgtggcagga gaggaggacc ttaagcctca gcacagcaac ttcaggggga
gagcctcgct gccaaaggac cagcttttga agggaaatgc tgcccttcag
atcacagacg tcaagctgca ggacgcaggc gtttactgct gcataatcag
ctacggtggt gcggactaca agcgaatcac gctgaaagtc aatgccccat
accgcaaaat caaccagaga atttccgtgg atccagccac ttctgagcat
gaactaatat gtcaggccga gggttatcca gaagctgagg taatctggac
aaacagtgac caccaacccg tgagtgggaa gagaagtgtc accacttccc
ggacagaggg gatgcttctc aatgtgacca gcagtctgag ggtcaacgcc
acagcgaatg atgttttcta ctgtacgttt tggagatcac agccagggca
aaaccacaca gcggagctga tcatcccaga actgcctgca acacatcctc
cacagaacag gactcactgg gtgcttctgg gatccatcct gttgttcctc
attgtagtgt ccacggtcct cctcttcttg agaaaacaag tgagaatgct
agatgtggag aaatgtggcg ttgaagatac aagctcaaaa aaccgaaatg
atacacaatt cgaggagacg taa
```

(SEQ ID NO:8)

Figure 7

```
atgatcttcc tcctgctaat gttgagcctg gaattgcagc ttcaccagat
agcagcttta ttcacagtga cagtccctaa ggaactgtac ataatagagc
atggcagcaa tgtgaccctg gaatgcaact ttgacactgg aagtcatgtg
aaccttggag caataacagc cagtttgcaa aaggtggaaa atgatacatc
cccacaccgt gaaagagcca ctttgctgga ggagcagctg cccctaggga
aggcctcgtt ccacatacct caagtccaag tgagggacga aggacagtac
caatgcataa tcatctatgg ggtcgcctgg gactacaagt acctgactct
gaaagtcaaa gcttcctaca ggaaaataaa cactcacatc ctaaaggttc
cagaaacaga tgaggtagag ctcacctgcc aggctacagg ttatcctctg
gcagaagtat cctggccaaa cgtcagcgtt cctgccaaca ccagccactc
caggacccct gaaggcctct accaggtcac cagtgttctg cgcctaaagc
cacccctgg cagaaacttc agctgtgtgt tctggaatac tcacgtgagg
gaacttactt tggccagcat tgaccttcaa agtcagatgg aacccaggac
ccatccaact tggctgcttc acattttcat cccctcctgc atcattgctt
tcattttcat agccacagtg atagccctaa gaaacaact ctgtcaaaag
ctgtattctt caaaagacac aacaaaaaga cctgtcacca caacaaagag
ggaagtgaac agtgctatct ga
```

(SEQ ID NO:9)

Figure 8

```
atgctgctcc tgctgccgat actgaacctg agcttacaac ttcatcctgt
agcagcttta ttcaccgtga cagcccctaa agaagtgtac accgtagacg
tcggcagcag tgtgagcctg gagtgcgatt ttgaccgcag agaatgcact
gaactggaag ggataagagc cagtttgcag aaggtagaaa atgatacgtc
tctgcaaagt gaaagagcca ccctgctgga ggagcagctg cccctgggaa
aggctttgtt ccacatccct agtgtccaag tgagagattc cgggcagtac
cgttgcctgg tcatctgcgg ggccgcctgg gactacaagt acctgacggt
gaaagtcaaa gcttcttaca tgaggataga cactaggatc ctggaggttc
caggtacagg ggaggtgcag cttacctgcc aggctagagg ttatccccta
gcagaagtgt cctggcaaaa tgtcagtgtt cctgccaaca ccagccacat
caggaccccc gaaggcctct accaggtcac cagtgttctg cgcctcaagc
ctcagcctag cagaaacttc agctgcatgt tctggaatgc tcacatgaag
gagctgactt cagccatcat tgaccctctg agtcggatgg aacccaaagt
ccccagaacg tggccacttc atgttttcat cccggcctgc accatcgctt
tgatcttcct ggccatagtg ataatccaga gaaagaggat ctag
```

(SEQ ID NO:10)

Figure 9

```
          A'                  B                      C                      C'
hCD86   L K  Q A Y . . . . . F N E T A D  P  Q F A N S Q N Q S   S E  V  F  Q D Q E N L    N E   Y
hCD80   I H  T K E . . . . . V K E V A T  S  G H . N V S V E E  A Q  R   Y  Q K E K . K    L T   M
hB7-H1  D L  V V E . . . . . Y G S N M T  E  K F P V E K Q L D  A A  I  Y  E M E D K N    Q F   H
mB7-H1  D L  V V E . . . . . Y G S N V T  E  R F P V E R E L D  L A  V  Y   K E D E Q    Q F
hB7-H2  K E  R A M . . . . . V G S D V E  S  A C P E G S R F D  N D  Y  Y  Q T S E S K    V T   H
hB7-H3  D P  V A L . . . . . V G T D A T  C  S P S P E P G F S  A Q  N  I  Q L T D T Q    H S   A
hPD-L2  E L  I I E . . . . . H G S N V T  E  N F D T G S H V N  G A  T  S  Q K . . . .    N D   S
mPD-L2  E V  T V D . . . . . V G S S V S  E  D F D R R E C T E  E G  R  S  Q K . . . .    N D   S
        26       31              37                   50              56          58        67 69
        28                       40                   50              56                      65 67

C"                   D                    E
hCD86   L G K E K F . D S V H S K  M G  T S  D S D S . . . . . W T  R  H N  Q I K  K
hCD80   S G D M N I . . . . W P E  K N  T I  D I T N . . . . N L S  V  L A  R P S  E
hB7-H1  . G E E D L . K V Q H S S  R Q  A R  L K D Q L S L G N A A  Q  T D  K L Q  A
mB7-H1  . G E E D L . K P Q H S N  R G  A S  P K D Q L L K G N A A  Q  T D  K L Q  A
hB7-H2  I P Q N S S L E N V D S R  R N  A L  S P A G L M R G D F S  R  F N  T P Q  E
hB7-H3  E G Q D Q G . . . . . S A  A N  T A  F P D L L A Q G N A S  R  Q R  R V A  E
hPD-L2  P H R E R A . . . . . T L  E E  L P  G K . . . . . . . A S  H  P Q  Q V R  E
mPD-L2  L Q S E R A . . . . . T L  E E  L P  G K . . . . . . . A L  H  P S  Q V R  S
        70            80                  90                  100         110
        71            80                  90                  100

F                    G
hCD86   L  Q G I  H H K K P T G M I R I H Q M N S E  S V L A   (SEQ ID NO:11)
hCD80   T  E  V  L K Y E K D A F K R E H L A E V T  S V K A   (SEQ ID NO:12)
hB7-H1  V  R  M  S Y G G A D Y K R I T V K V N A P  N K I N   (SEQ ID NO:13)
mB7-H1  V   I   S Y G G A D Y K R I T L K V N A P  R K I N   (SEQ ID NO:14)
hB7-H2  K  H  L  L S Q S . L G F Q E V L S V E V T  H V A A   (SEQ ID NO:15)
hB7-H3  S  T  F  S I R D P G S A A V S L Q V A A P  S K P S   (SEQ ID NO:16)
hPD-L2  Q  Q  I  I Y G V . A W D Y K Y L T L K V K  S Y R K   (SEQ ID NO:17)
mPD-L2  Q  R  L  I C G A . A W D Y K Y L T V K V K  S Y M R   (SEQ ID NO:18)
                115          124         129         138
        101     105          111         120         125
```

SEQUENCE LISTING

```
<160> NUMBER OF SEQ ID NOS: 22

<210> SEQ ID NO 1
<211> LENGTH: 6
<212> TYPE: PRT
<213> ORGANISM: Homo sapiens

<400> SEQUENCE: 1

Met Tyr Pro Pro Pro Tyr
1               5

<210> SEQ ID NO 2
<211> LENGTH: 6
<212> TYPE: PRT
<213> ORGANISM: Homo sapiens

<400> SEQUENCE: 2

Phe Asp Pro Pro Pro Phe
1               5

<210> SEQ ID NO 3
<211> LENGTH: 290
<212> TYPE: PRT
<213> ORGANISM: Homo sapiens

<400> SEQUENCE: 3

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
```

```
                    100                 105                 110
Arg Cys Met Ile Ser Tyr Gly Gly Ala Asp Tyr Lys Arg Ile Thr Val
            115                 120                 125
Lys Val Asn Ala Pro Tyr Asn Lys Ile Asn Gln Arg Ile Leu Val Val
        130                 135                 140
Asp Pro Val Thr Ser Glu His Glu Leu Thr Cys Gln Ala Glu Gly Tyr
145                 150                 155                 160
Pro Lys Ala Glu Val Ile Trp Thr Ser Ser Asp His Gln Val Leu Ser
                165                 170                 175
Gly Lys Thr Thr Thr Thr Asn Ser Lys Arg Glu Glu Lys Leu Phe Asn
            180                 185                 190
Val Thr Ser Thr Leu Arg Ile Asn Thr Thr Thr Asn Glu Ile Phe Tyr
        195                 200                 205
Cys Thr Phe Arg Arg Leu Asp Pro Glu Glu Asn His Thr Ala Glu Leu
210                 215                 220
Val Ile Pro Glu Leu Pro Leu Ala His Pro Pro Asn Glu Arg Thr His
225                 230                 235                 240
Leu Val Ile Leu Gly Ala Ile Leu Leu Cys Leu Gly Val Ala Leu Thr
                245                 250                 255
Phe Ile Phe Arg Leu Arg Lys Gly Arg Met Met Asp Val Lys Lys Cys
            260                 265                 270
Gly Ile Gln Asp Thr Asn Ser Lys Lys Gln Ser Asp Thr His Leu Glu
        275                 280                 285
Glu Thr
    290

<210> SEQ ID NO 4
<211> LENGTH: 290
<212> TYPE: PRT
<213> ORGANISM: Mus musculus

<400> SEQUENCE: 4

Met Arg Ile Phe Ala Gly Ile Ile Phe Thr Ala Cys Cys His Leu Leu
1               5                   10                  15
Arg Ala Phe Thr Ile Thr Ala Pro Lys Asp Leu Tyr Val Val Glu Tyr
            20                  25                  30
Gly Ser Asn Val Thr Met Glu Cys Arg Phe Pro Val Glu Arg Glu Leu
        35                  40                  45
Asp Leu Leu Ala Leu Val Val Tyr Trp Glu Lys Glu Asp Glu Gln Val
    50                  55                  60
Ile Gln Phe Val Ala Gly Glu Glu Asp Leu Lys Pro Gln His Ser Asn
65                  70                  75                  80
Phe Arg Gly Arg Ala Ser Leu Pro Lys Asp Gln Leu Leu Lys Gly Asn
                85                  90                  95
Ala Ala Leu Gln Ile Thr Asp Val Lys Leu Gln Asp Ala Gly Val Tyr
            100                 105                 110
Cys Cys Ile Ile Ser Tyr Gly Gly Ala Asp Tyr Lys Arg Ile Thr Leu
        115                 120                 125
Lys Val Asn Ala Pro Tyr Arg Lys Ile Asn Gln Arg Ile Ser Val Asp
    130                 135                 140
Pro Ala Thr Ser Glu His Glu Leu Ile Cys Gln Ala Glu Gly Tyr Pro
145                 150                 155                 160
Glu Ala Glu Val Ile Trp Thr Asn Ser Asp His Gln Pro Val Ser Gly
                165                 170                 175
Lys Arg Ser Val Thr Thr Ser Arg Thr Glu Gly Met Leu Leu Asn Val
```

```
                              180                 185                 190
Thr Ser Ser Leu Arg Val Asn Ala Thr Ala Asn Asp Val Phe Tyr Cys
            195                 200                 205
Thr Phe Trp Arg Ser Gln Pro Gly Gln Asn His Thr Ala Glu Leu Ile
        210                 215                 220
Ile Pro Glu Leu Pro Ala Thr His Pro Pro Gln Asn Arg Thr His Trp
225                 230                 235                 240
Val Leu Leu Gly Ser Ile Leu Leu Phe Leu Ile Val Val Ser Thr Val
            245                 250                 255
Leu Leu Phe Leu Arg Lys Gln Val Arg Met Leu Asp Val Glu Lys Cys
        260                 265                 270
Gly Val Glu Asp Thr Ser Ser Lys Asn Arg Asn Asp Thr Gln Phe Glu
            275                 280                 285
Glu Thr
    290

<210> SEQ ID NO 5
<211> LENGTH: 273
<212> TYPE: PRT
<213> ORGANISM: Homo sapiens

<400> SEQUENCE: 5

Met Ile Phe Leu Leu Leu Met Leu Ser Leu Glu Leu Gln Leu His Gln
1               5                   10                  15
Ile Ala Ala Leu Phe Thr Val Thr Val Pro Lys Glu Leu Tyr Ile Ile
            20                  25                  30
Glu His Gly Ser Asn Val Thr Leu Glu Cys Asn Phe Asp Thr Gly Ser
        35                  40                  45
His Val Asn Leu Gly Ala Ile Thr Ala Ser Leu Gln Lys Val Glu Asn
    50                  55                  60
Asp Thr Ser Pro His Arg Glu Arg Ala Thr Leu Leu Glu Glu Gln Leu
65                  70                  75                  80
Pro Leu Gly Lys Ala Ser Phe His Ile Pro Gln Val Gln Val Arg Asp
            85                  90                  95
Glu Gly Gln Tyr Gln Cys Ile Ile Ile Tyr Gly Val Ala Trp Asp Tyr
            100                 105                 110
Lys Tyr Leu Thr Leu Lys Val Lys Ala Ser Tyr Arg Lys Ile Asn Thr
        115                 120                 125
His Ile Leu Lys Val Pro Glu Thr Asp Glu Val Glu Leu Thr Cys Gln
    130                 135                 140
Ala Thr Gly Tyr Pro Leu Ala Glu Val Ser Trp Pro Asn Val Ser Val
145                 150                 155                 160
Pro Ala Asn Thr Ser His Ser Arg Thr Pro Glu Gly Leu Tyr Gln Val
            165                 170                 175
Thr Ser Val Leu Arg Leu Lys Pro Pro Pro Gly Arg Asn Phe Ser Cys
        180                 185                 190
Val Phe Trp Asn Thr His Val Arg Glu Leu Thr Leu Ala Ser Ile Asp
        195                 200                 205
Leu Gln Ser Gln Met Glu Pro Arg Thr His Pro Thr Trp Leu Leu His
    210                 215                 220
Ile Phe Ile Pro Ser Cys Ile Ile Ala Phe Ile Phe Ile Ala Thr Val
225                 230                 235                 240
Ile Ala Leu Arg Lys Gln Leu Cys Gln Lys Leu Tyr Ser Ser Lys Asp
            245                 250                 255
Thr Thr Lys Arg Pro Val Thr Thr Thr Lys Arg Glu Val Asn Ser Ala
```

Ile

<210> SEQ ID NO 6
<211> LENGTH: 247
<212> TYPE: PRT
<213> ORGANISM: Mus musculus

<400> SEQUENCE: 6

```
Met Leu Leu Leu Leu Pro Ile Leu Asn Leu Ser Gln Leu His Pro
 1               5                  10                  15

Val Ala Ala Leu Phe Thr Val Thr Ala Pro Lys Glu Val Tyr Thr Val
            20                  25                  30

Asp Val Gly Ser Ser Val Ser Leu Glu Cys Asp Phe Asp Arg Arg Glu
            35                  40                  45

Cys Thr Glu Leu Glu Gly Ile Arg Ala Ser Leu Gln Lys Val Glu Asn
        50                  55                  60

Asp Thr Ser Leu Gln Ser Glu Arg Ala Thr Leu Glu Glu Gln Leu
 65                  70                  75                  80

Pro Leu Gly Lys Ala Leu Phe His Ile Pro Ser Val Gln Val Arg Asp
                85                  90                  95

Ser Gly Gln Tyr Arg Cys Leu Val Ile Cys Gly Ala Ala Trp Asp Tyr
            100                 105                 110

Lys Tyr Leu Thr Val Lys Val Lys Ala Ser Tyr Met Arg Ile Asp Thr
            115                 120                 125

Arg Ile Leu Glu Val Pro Gly Thr Gly Glu Val Gln Leu Thr Cys Gln
    130                 135                 140

Ala Arg Gly Tyr Pro Leu Ala Glu Val Ser Trp Gln Asn Val Ser Val
145                 150                 155                 160

Pro Ala Asn Thr Ser His Ile Arg Thr Pro Glu Gly Leu Tyr Gln Val
                165                 170                 175

Thr Ser Val Leu Arg Leu Lys Pro Gln Pro Ser Arg Asn Phe Ser Cys
                180                 185                 190

Met Phe Trp Asn Ala His Met Lys Glu Leu Thr Ser Ala Ile Ile Asp
            195                 200                 205

Pro Leu Ser Arg Met Glu Pro Lys Val Pro Arg Thr Trp Pro Leu His
    210                 215                 220

Val Phe Ile Pro Ala Cys Thr Ile Ala Leu Ile Phe Leu Ala Ile Val
225                 230                 235                 240

Ile Ile Gln Arg Lys Arg Ile
                245
```

<210> SEQ ID NO 7
<211> LENGTH: 873
<212> TYPE: DNA
<213> ORGANISM: Homo sapiens

<400> SEQUENCE: 7

```
atgaggatat tgctgtctt tatattcatg acctactggc atttgctgaa cgcatttact      60
gtcacggttc ccaaggacct atatgtggta gagtatggta gcaatatgac aattgaatgc     120
aaattcccag tagaaaaaca attagacctg ctgcactaa ttgtctattg ggaaatggag      180
gataagaaca ttattcaatt tgtgcatgga gaggaagacc tgaaggttca gcatagtagc     240
tacagacaga gggcccggct gttgaaggac cagctctccc tgggaaatgc tgcacttcag     300
atcacagatg tgaaattgca ggatgcaggg gtgtaccgct gcatgatcag ctatggtggt     360
```

|  |  |
|---|---|
| gccgactaca agcgaattac tgtgaaagtc aatgccccat acaacaaaat caaccaaaga | 420 |
| attttggttg tggatccagt cacctctgaa catgaactga catgtcaggc tgagggctac | 480 |
| cccaaggccg aagtcatctg acaagcagt gaccatcaag tcctgagtgg taagaccacc | 540 |
| accaccaatt ccaagagaga ggagaagctt ttcaatgtga ccagcacact gagaatcaac | 600 |
| acaacaacta atgagatttt ctactgcact tttaggagat tagatcctga ggaaaaccat | 660 |
| acagctgaat tggtcatccc agaactacct ctggcacatc ctccaaatga aaggactcac | 720 |
| ttggtaattc tgggagccat cttattatgc cttggtgtag cactgacatt catcttccgt | 780 |
| ttaagaaaag ggagaatgat ggatgtgaaa aaatgtggca tccaagatac aaactcaaag | 840 |
| aagcaaagtg atacacattt ggaggagacg taa | 873 |

<210> SEQ ID NO 8
<211> LENGTH: 873
<212> TYPE: DNA
<213> ORGANISM: Mus musculus

<400> SEQUENCE: 8

|  |  |
|---|---|
| atgaggatat ttgctggcat tatattcaca gcctgctgtc acttgctacg ggcgtttact | 60 |
| atcacggctc caaaggactt gtacgtggtg gagtatggca gcaacgtcac gatggagtgc | 120 |
| agattccctg tagaacggga gctggacctg cttgcgttag tggtgtactg ggaaaaggaa | 180 |
| gatgagcaag tgattcagtt tgtggcagga gaggaggacc ttaagcctca gcacagcaac | 240 |
| ttcaggggga gagcctcgct gccaaaggac cagcttttga agggaaatgc tgcccttcag | 300 |
| atcacagacg tcaagctgca ggacgcaggc gtttactgct gcataatcag ctacggtggt | 360 |
| gcggactaca agcgaatcac gctgaaagtc aatgccccat accgcaaaat caaccagaga | 420 |
| atttccgtgg atccagccac ttctgagcat gaactaatat gtcaggccga gggttatcca | 480 |
| gaagctgagg taatctggac aaacagtgac caccaacccg tgagtgggaa gagaagtgtc | 540 |
| accacttccc ggacagaggg gatgcttctc aatgtgacca gcagtctgag ggtcaacgcc | 600 |
| acagcgaatg atgttttcta ctgtacgttt tggagatcac agccagggca aaaccacaca | 660 |
| gcggagctga tcatcccaga actgcctgca acacatcctc cacagaacag gactcactgg | 720 |
| gtgcttctgg gatccatcct gttgttcctc attgtagtgt ccacggtcct cctcttcttg | 780 |
| agaaaacaag tgagaatgct agatgtggag aaatgtggcg ttgaagatac aagctcaaaa | 840 |
| aaccgaaatg atacacaatt cgaggagacg taa | 873 |

<210> SEQ ID NO 9
<211> LENGTH: 822
<212> TYPE: DNA
<213> ORGANISM: Homo sapiens

<400> SEQUENCE: 9

|  |  |
|---|---|
| atgatcttcc tcctgctaat gttgagcctg gaattgcagc ttcaccagat agcagcttta | 60 |
| ttcacagtga cagtccctaa ggaactgtac ataatagagc atggcagcaa tgtgaccctg | 120 |
| gaatgcaact ttgacactgg aagtcatgtg aaccttggag caataacagc cagttttgcaa | 180 |
| aaggtggaaa atgatacatc cccacaccgt gaaagagcca ctttgctgga ggagcagctg | 240 |
| cccctaggga aggcctcgtt ccacatacct caagtccaag tgaggacga aggacagtac | 300 |
| caatgcataa tcatctatgg ggtcgcctgg gactacaagt acctgactct gaaagtcaaa | 360 |
| gcttcctaca ggaaaataaa cactcacatc ctaaaggttc cagaaacaga tgaggtagag | 420 |
| ctcacctgcc aggctacagg ttatcctctg gcagaagtat cctggccaaa cgtcagcgtt | 480 |

```
cctgccaaca ccagccactc caggacccct gaaggcctct accaggtcac cagtgttctg    540
cgcctaaagc caccccctgg cagaaacttc agctgtgtgt tctggaatac tcacgtgagg    600
gaacttactt tggccagcat tgaccttcaa agtcagatgg aacccaggac ccatccaact    660
tggctgcttc acattttcat cccctcctgc atcattgctt tcattttcat agccacagtg    720
atagccctaa gaaaacaact ctgtcaaaag ctgtattctt caaaagacac aacaaaaaga    780
cctgtcacca acaaagag ggaagtgaac agtgctatct ga    822

<210> SEQ ID NO 10
<211> LENGTH: 744
<212> TYPE: DNA
<213> ORGANISM: Mus musculus

<400> SEQUENCE: 10
atgctgctcc tgctgccgat actgaacctg agcttacaac ttcatcctgt agcagcttta     60
ttcaccgtga cagcccctaa agaagtgtac accgtagacg tcggcagcag tgtgagcctg    120
gagtgcgatt ttgaccgcag agaatgcact gaactggaag ggataagagc cagtttgcag    180
aaggtagaaa atgatacgtc tctgcaaagt gaaagagcca ccctgctgga ggagcagctg    240
cccctgggaa aggctttgtt ccacatccct agtgtccaag tgagagattc cgggcagtac    300
cgttgcctgg tcatctgcgg ggccgcctgg gactacaagt acctgacggt gaaagtcaaa    360
gcttcttaca tgaggataga cactaggatc ctggaggttc aggtacaggg gaggtgcag    420 cttacctgcc aggctagagg ttatccccta gcagaagtgt cctggcaaaa tgtcagtgtt    480
cctgccaaca ccagccacat caggaccccc gaaggcctct accaggtcac cagtgttctg    540
cgcctcaagc ctcagcctag cagaaacttc agctgcatgt tctggaatgc tcacatgaag    600
gagctgactt cagccatcat tgaccctctg agtcggatgg aacccaaagt ccccagaacg    660
tggccacttc atgttttcat cccggcctgc accatcgctt tgatcttcct ggccatagtg    720
ataatccaga gaaagaggat ctag    744

<210> SEQ ID NO 11
<211> LENGTH: 109
<212> TYPE: PRT
<213> ORGANISM: Homo sapiens

<400> SEQUENCE: 11

Leu Lys Ile Gln Ala Tyr Phe Asn Glu Thr Ala Asp Leu Pro Cys Gln
  1               5                  10                  15

Phe Ala Asn Ser Gln Asn Gln Ser Leu Ser Glu Leu Val Val Phe Trp
             20                  25                  30

Gln Asp Gln Glu Asn Leu Val Leu Asn Glu Val Tyr Leu Gly Lys Glu
         35                  40                  45

Lys Phe Asp Ser Val His Ser Lys Tyr Met Gly Arg Thr Ser Phe Asp
     50                  55                  60

Ser Asp Ser Trp Thr Leu Arg Leu His Asn Leu Gln Ile Lys Asp Lys
 65                  70                  75                  80

Gly Leu Tyr Gln Cys Ile Ile His His Lys Lys Pro Thr Gly Met Ile
                 85                  90                  95

Arg Ile His Gln Met Asn Ser Glu Leu Ser Val Leu Ala
            100                 105

<210> SEQ ID NO 12
<211> LENGTH: 105
<212> TYPE: PRT
<213> ORGANISM: Homo sapiens
```

<400> SEQUENCE: 12

```
Ile His Val Thr Lys Glu Val Lys Glu Val Ala Thr Leu Ser Cys Gly
  1               5                  10                  15

His Asn Val Ser Val Glu Glu Leu Ala Gln Thr Arg Ile Tyr Trp Gln
             20                  25                  30

Lys Glu Lys Lys Met Val Leu Thr Met Met Ser Gly Asp Met Asn Ile
         35                  40                  45

Trp Pro Glu Tyr Lys Asn Arg Thr Ile Phe Asp Ile Thr Asn Asn Leu
     50                  55                  60

Ser Ile Val Ile Leu Ala Leu Arg Pro Ser Asp Glu Gly Thr Tyr Glu
 65                  70                  75                  80

Cys Val Val Leu Lys Tyr Glu Lys Asp Ala Phe Lys Arg Glu His Leu
                 85                  90                  95

Ala Glu Val Thr Leu Ser Val Lys Ala
            100                 105
```

<210> SEQ ID NO 13
<211> LENGTH: 113
<212> TYPE: PRT
<213> ORGANISM: Homo sapiens

<400> SEQUENCE: 13

```
Asp Leu Tyr Val Val Glu Tyr Gly Ser Asn Met Thr Ile Glu Cys Lys
  1               5                  10                  15

Phe Pro Val Glu Lys Gln Leu Asp Leu Ala Ala Leu Ile Val Tyr Trp
             20                  25                  30

Glu Met Glu Asp Lys Asn Ile Ile Gln Phe Val His Gly Glu Glu Asp
         35                  40                  45

Leu Lys Val Gln His Ser Ser Tyr Arg Gln Arg Ala Arg Leu Leu Lys
     50                  55                  60

Asp Gln Leu Ser Leu Gly Asn Ala Ala Leu Gln Ile Thr Asp Val Lys
 65                  70                  75                  80

Leu Gln Asp Ala Gly Val Tyr Arg Cys Met Ile Ser Tyr Gly Gly Ala
                 85                  90                  95

Asp Tyr Lys Arg Ile Thr Val Lys Val Asn Ala Pro Tyr Asn Lys Ile
            100                 105                 110

Asn
```

<210> SEQ ID NO 14
<211> LENGTH: 113
<212> TYPE: PRT
<213> ORGANISM: Mus musculus

<400> SEQUENCE: 14

```
Asp Leu Tyr Val Val Glu Tyr Gly Ser Asn Val Thr Met Glu Cys Arg
  1               5                  10                  15

Phe Pro Val Glu Arg Glu Leu Asp Leu Leu Ala Leu Val Val Tyr Trp
             20                  25                  30

Glu Lys Glu Asp Glu Gln Val Ile Gln Phe Val Ala Gly Glu Glu Asp
         35                  40                  45

Leu Lys Pro Gln His Ser Asn Phe Arg Gly Arg Ala Ser Leu Pro Lys
     50                  55                  60

Asp Gln Leu Leu Lys Gly Asn Ala Ala Leu Gln Ile Thr Asp Val Lys
 65                  70                  75                  80

Leu Gln Asp Ala Gly Val Tyr Cys Cys Ile Ile Ser Tyr Gly Gly Ala
                 85                  90                  95
```

```
Asp Tyr Lys Arg Ile Thr Leu Lys Val Asn Ala Pro Tyr Arg Lys Ile
            100                 105                 110
Asn

<210> SEQ ID NO 15
<211> LENGTH: 114
<212> TYPE: PRT
<213> ORGANISM: Homo sapiens

<400> SEQUENCE: 15

Lys Glu Val Arg Ala Met Val Gly Ser Asp Val Glu Leu Ser Cys Ala
 1               5                  10                  15

Cys Pro Glu Gly Ser Arg Phe Asp Leu Asn Asp Val Tyr Val Tyr Trp
             20                  25                  30

Gln Thr Ser Glu Ser Lys Thr Val Thr Tyr His Ile Pro Gln Asn
         35                  40                  45

Ser Ser Leu Glu Asn Val Asp Ser Arg Tyr Arg Asn Arg Ala Leu Met
50                  55                  60

Ser Pro Ala Gly Leu Met Arg Gly Asp Phe Ser Leu Arg Leu Phe Asn
65                  70                  75                  80

Val Thr Pro Gln Asp Glu Gln Lys Phe His Cys Leu Val Leu Ser Gln
             85                  90                  95

Ser Leu Gly Phe Gln Glu Val Leu Ser Val Glu Val Thr Leu His Val
            100                 105                 110

Ala Ala

<210> SEQ ID NO 16
<211> LENGTH: 110
<212> TYPE: PRT
<213> ORGANISM: Homo sapiens

<400> SEQUENCE: 16

Asp Pro Val Val Ala Leu Val Gly Thr Asp Ala Thr Leu Cys Cys Ser
 1               5                  10                  15

Pro Ser Pro Glu Pro Gly Phe Ser Leu Ala Gln Leu Asn Leu Ile Trp
             20                  25                  30

Gln Leu Thr Asp Thr Gln Leu Val His Ser Phe Ala Glu Gly Gln Asp
         35                  40                  45

Gln Gly Ser Ala Tyr Ala Asn Arg Thr Ala Leu Phe Pro Asp Leu Leu
50                  55                  60

Ala Gln Gly Asn Ala Ser Leu Arg Leu Gln Arg Val Arg Val Ala Asp
65                  70                  75                  80

Glu Gly Ser Phe Thr Cys Phe Val Ser Ile Arg Asp Phe Gly Ser Ala
             85                  90                  95

Ala Val Ser Leu Gln Val Ala Ala Pro Tyr Ser Lys Pro Ser
            100                 105                 110

<210> SEQ ID NO 17
<211> LENGTH: 98
<212> TYPE: PRT
<213> ORGANISM: Homo sapiens

<400> SEQUENCE: 17

Glu Leu Tyr Ile Ile Glu His Gly Ser Asn Val Thr Leu Glu Cys Asn
 1               5                  10                  15

Phe Asp Thr Gly Ser His Val Asn Leu Gly Ala Ile Thr Ala Ser Leu
             20                  25                  30
```

-continued

```
Gln Lys Val Glu Asn Asp Thr Ser Pro His Arg Glu Arg Ala Thr Leu
            35                  40                  45

Leu Glu Glu Gln Leu Pro Leu Gly Lys Ala Ser Phe His Ile Pro Gln
 50                  55                  60

Val Gln Val Arg Asp Glu Gly Gln Tyr Gln Cys Ile Ile Ile Tyr Gly
 65                  70                  75                  80

Val Ala Trp Asp Tyr Lys Tyr Leu Thr Leu Lys Val Lys Ala Ser Tyr
                 85                  90                  95

Arg Lys
```

<210> SEQ ID NO 18
<211> LENGTH: 98
<212> TYPE: PRT
<213> ORGANISM: Mus musculus

<400> SEQUENCE: 18

```
Glu Val Tyr Thr Val Asp Val Gly Ser Ser Val Ser Leu Glu Cys Asp
 1               5                  10                  15

Phe Asp Arg Arg Glu Cys Thr Glu Leu Glu Gly Ile Arg Ala Ser Leu
                20                  25                  30

Gln Lys Val Glu Asn Asp Thr Ser Leu Gln Ser Glu Arg Ala Thr Leu
            35                  40                  45

Leu Glu Glu Gln Leu Pro Leu Gly Lys Ala Leu Phe Asp Ile Pro Ser
 50                  55                  60

Val Gln Val Arg Asp Ser Gly Gln Tyr Arg Cys Leu Val Ile Cys Gly
 65                  70                  75                  80

Ala Ala Trp Asp Tyr Lys Tyr Leu Thr Val Lys Val Lys Ala Ser Tyr
                 85                  90                  95

Met Arg
```

<210> SEQ ID NO 19
<211> LENGTH: 25
<212> TYPE: PRT
<213> ORGANISM: Artificial Sequence
<220> FEATURE:
<223> OTHER INFORMATION: Consensus

<400> SEQUENCE: 19

```
Met Ala Ile Ser Gly Val Pro Val Leu Gly Phe Phe Ile Ile Ala Val
 1               5                  10                  15

Leu Met Ser Ala Gln Glu Ser Trp Ala
                20                  25
```

<210> SEQ ID NO 20
<211> LENGTH: 5
<212> TYPE: PRT
<213> ORGANISM: Artificial Sequence
<220> FEATURE:
<223> OTHER INFORMATION: Consensus

<400> SEQUENCE: 20

```
Lys Phe Glu Arg Gln
 1               5
```

<210> SEQ ID NO 21
<211> LENGTH: 15
<212> TYPE: PRT
<213> ORGANISM: Artificial Sequence
<220> FEATURE:
<223> OTHER INFORMATION: Consensus

<400> SEQUENCE: 21

```
Met Asp Gln Arg Asp Leu Ile Ser Asn Asn Glu Gln Leu Pro
1               5                   10                  15

<210> SEQ ID NO 22
<211> LENGTH: 4
<212> TYPE: PRT
<213> ORGANISM: Artificial Sequence
<220> FEATURE:
<223> OTHER INFORMATION: Consensus

<400> SEQUENCE: 22

Lys Asp Glu Leu
1
```

US 8,039,589 B1

B7-DC VARIANTS

CROSS-REFERENCE TO RELATED APPLICATIONS

This application is a divisional of U.S. Ser. No. 10/679,775, filed Oct. 6, 2003, which claims priority from U.S. Provisional Application Ser. No. 60/416,203, filed Oct. 4, 2002.

STATEMENT AS TO FEDERALLY SPONSORED RESEARCH

This invention was made with government support under grant no. CA97085, awarded by the National Institutes of Health. The government has certain rights in the invention.

TECHNICAL FIELD

This invention relates to materials and methods for enhancing T cell activation.

BACKGROUND

Antigen-specific activation and proliferation of lymphocytes are regulated by both positive and negative signals from costimulatory molecules. The most extensively characterized T cell costimulatory pathway is B7-CD28, in which B7-1 (CD80) and B7-2 (CD86) each can engage the stimulatory CD28 receptor and the inhibitory CTLA-4 (CD152) receptor. In conjunction with signaling through the T cell receptor, CD28 ligation increases antigen-specific proliferation of T cells, enhances production of cytokines, stimulates differentiation and effector function, and promotes survival of T cells (Lenshow et al. (1996) *Annu. Rev. Immunol.* 14:233-258; Chambers and Allison (1997) *Curr. Opin. Immunol.* 9:396-404; and Rathmell and Thompson (1999) *Annu. Rev. Immunol.* 17:781-828). In contrast, signaling through CTLA-4 is thought to deliver a negative signal that inhibits T cell proliferation, IL-2 production, and cell cycle progression (Krummel and Allison (1996) *J. Exp. Med.* 183:2533-2540; and Walunas et al. (1996) *J. Exp. Med.* 183:2541-2550). Other members of the B7 family include B7-H1 (Dong et al. (1999) *Nature Med.* 5:1365-1369; and Freeman et al. (2000) *J. Exp. Med.* 192:1-9), B7-DC (Tseng et al. (2001) *J. Exp. Med.* 193:839-846; and Latchman et al. (2001) *Nature Immunol.* 2:261-268), B7-H2 (Wang et al. (2000) *Blood* 96:2808-2813; Swallow et al. (1999) *Immunity* 11:423-432; and Yoshinaga et al. (1999) *Nature* 402:827-832), and B7-H3 (Chapoval et al. (2001) *Nature Immunol.* 2:269-274). B7-H1 and B7-DC are ligands for PD-1, B7-H2 is a ligand for ICOS, and B7-H3 remains at this time an orphan ligand (Dong et al. (2003) *Immunol. Res.* 28:39-48).

B7 family molecules are expressed on the cell surface as homodimers with a membrane proximal constant IgC domain and a membrane distal IgV domain. Receptors for these ligands share a common extracellular IgV-like domain. Interactions of receptor-ligand pairs are mediated predominantly through residues in the IgV domains of the ligands and receptors (Schwartz et al. (2002) *Nature Immunol.* 3:427-434). In general, IgV domains are described as having two sheets that each contain a layer of β-strands (Williams and Barclay (1988) *Annu. Rev. Immunol.* 6:381-405). The front and back sheets of CTLA-4 contain strands A'GFCC' and ABEDC," respectively (Ostrov et al. (2000) *Science* 290:816-819), whereas the front and back sheets of the B7 IgV domains are composed of strands AGFCC'C" and BED, respectively (Schwartz et al. (2001) *Nature* 410:604-608; Stamper et al (2001) *Nature* 410:608-611; and Ikemizu et al. (2000) *Immunity* 12:51-60). Crystallographic analysis revealed that the CTLA-4/B7 binding interface is dominated by the interaction of the CDR3-analogous loop from CTLA-4, composed of a MYPPPY (SEQ ID NO:1) motif, with a surface on B7 formed predominately by the G, F, C, C' and C" strands (Schwartz et al. (2001) supra; and Stamper et al. supra). Data from amino acid homologies, mutation, and computer modeling provide support for the concept that this motif also is a major B7-binding site for CD28 (Bajorath et al. (1997) *J. Mol. Graph. Model.* 15:135-139). Although the MYPPPY motif is not conserved in ICOS, studies have indicated that a related motif having the sequence FDPPPF (SEQ ID NO:2) and located at the analogous position is a major determinant for binding of ICOS to B7-H2 (Wand et al. (2002) *J. Exp. Med.* 195:1033-1041).

B7-H1 (also called PD-L1) and B7-DC (also called PD-L2) are relatively new members of the B7 family, and have amino acid sequences that are about 34% identical to each other. Human and mouse orthologues of these molecules share about 70% amino acid identity (i.e., the human and mouse B7-H1 amino acid sequences are about 70% identical, and the human and mouse B7-DC amino acid sequences are about 70% identical). While B7-H1 and B7-DC transcripts are found in various tissues (Dong et al. (1999) supra; Latchman et al. supra; and Tamura (2001) *Blood* 97:1809-1816), the expression profiles of the proteins are quite distinct. Expression of B7-H1 protein, although essentially not found in normal tissues other than macrophage-like cells, can be induced in a variety of tissues and cell types (Dong et al. (1999) supra; Tamura et al. supra; and Ishida et al. (2000) *Immunol. Lett.* 84:57-62). In contrast, B7-DC is expressed only in dendritic cells and monocytes (Tseng et al. supra; and Ishida et al. supra).

SUMMARY

The invention provides materials and methods for enhancing a costimulatory response, enhancing T cell activation, and inhibiting interaction between a costimulatory molecule and PD-1. For example, the invention provides purified variant costimulatory polypeptides that have altered binding affinity for PD-1, but that retain substantial costimulatory activity. Since it is likely that the interaction of costimulatory molecules such as B7-H1 and B7-DC with PD-1 suppresses an immune response, variant B7-H1 and variant B7-DC polypeptides with decreased binding affinity for PD-1 can be useful to enhance an immune response.

Methods of the invention can be used to enhance an immune response, enhance T cell activation, or inhibit binding of costimulatory polypeptides to PD-1, for example. Such methods can involve contacting a T cell with any of the purified variant costimulatory polypeptides or fragments provided herein. The T cell can be contacted in vitro or in vivo (e.g., in a mammal such as a mouse or a human). In some embodiments, the T cell can be contacted with a host cell [e.g., an antigen presenting cell (APC)] transfected or transduced with a nucleic acid encoding a polypeptide of the invention. If the T cell is contacted in a mammal, the host cell can be from that mammal or from another mammal. For example, the host cell can be from another mammal of the same species (e.g., another mammal that is histocompatible with the mammal to which the cells are being administered).

In one aspect, the invention provides a purified variant costimulatory polypeptide, wherein the variant polypeptide is a variant of a wild-type costimulatory polypeptide that binds to PD-1 and has reduced binding affinity for PD-1 compared to the wild-type costimulatory polypeptide, wherein the binding affinity is reduced by at least 50 percent as compared to the binding affinity of the wild-type costimulatory polypeptide, and wherein the costimulatory polypeptide retains substantial costimulatory activity. The variant costimulatory polypeptide can contain a substitution of one or more (e.g., two, three, four, five, six, seven, eight, nine, ten, or more than ten) amino acids of the wild-type polypeptide.

The wild-type polypeptide can be a B7-H1 polypeptide [e.g., murine B7-H1 (SEQ ID NO:4)]. The purified variant costimulatory polypeptide can contain a substitution of the amino acid at position 67 of SEQ ID NO:4. The substitution can involve replacing the amino acid at position 67 of SEQ ID NO:4 with an alanine residue. The purified variant costimulatory polypeptide can contain a substitution of the amino acid at position 126 of SEQ ID NO:4. The substitution can involve replacing the amino acid at position 126 of SEQ ID NO:4 with an alanine residue. The purified variant costimulatory polypeptide can contain a substitution of the amino acid at position 37 of SEQ ID NO:4. The substitution can involve replacing the amino acid at position 37 of SEQ ID NO:4 with a tyrosine residue. The purified variant costimulatory polypeptide can contain a substitution of the amino acid at position 115 of SEQ ID NO:4. The substitution can involve replacing the amino acid at position 115 of SEQ ID NO:4 with an alanine residue. The purified variant costimulatory polypeptide can contain a substitution of the amino acid at position 124 of SEQ ID NO:4. The substitution can involve replacing the amino acid at position 124 of SEQ m NO:4 with a serine residue.

The wild-type polypeptide can be a B7-DC polypeptide [e.g., murine B7-DC (SEQ ID NO:6)]. The purified variant costimulatory polypeptide can contain a substitution of the amino acid at position 111 of SEQ ID NO:6. The substitution can involve replacing the amino acid at position 111 of SEQ ID NO:6 with a serine residue. The purified variant costimulatory polypeptide can contain a substitution of the amino acid at position 113 of SEQ ID NO:6. The substitution can involve replacing the amino acid at position 113 of SEQ ID NO:6 with a serine residue. The purified variant costimulatory polypeptide can contain a substitution of the amino acid at position 56 of SEQ ID NO:6. The substitution can involve replacing the amino acid at position 56 of SEQ ID NO:6 with a serine residue. The purified variant costimulatory polypeptide can contain a substitution of the amino acid at position 67 of SEQ ID NO:6. The substitution can involve replacing the amino acid at position 67 of SEQ ID NO:6 with a tyrosine residue. The purified variant costimulatory polypeptide can contain a substitution of the amino acid at position 71 of SEQ ID NO:6. The substitution can involve replacing the amino acid at position 71 of SEQ ID NO:6 with a serine residue. The purified variant costimulatory polypeptide can contain a substitution of the amino acid at position 101 of SEQ ID NO:6. The substitution can involve replacing the amino acid at position 101 of SEQ ID NO:6 with a serine residue. The purified variant costimulatory polypeptide can contain a substitution of the amino acid at position 105 of SEQ ID NO:6. The substitution can involve replacing the amino acid at position 105 of SEQ ID NO:6 with an alanine residue.

The invention also provides a purified variant costimulatory polypeptide, wherein the variant polypeptide is a variant of a wild-type costimulatory polypeptide that binds to PD-1 and has increased binding affinity for PD-1 compared to the wild-type costimulatory polypeptide, wherein the affinity is increased by at least 50 percent as compared to the affinity of the wild-type costimulatory polypeptide, and wherein the costimulatory polypeptide retains substantial costimulatory activity. The variant costimulatory polypeptide can contain a substitution of one or more amino acids of the wild-type polypeptide. The wild-type polypeptide can be a B7-H1 polypeptide [e.g., murine B7-H1 (SEQ ID NO:4)]. The purified variant costimulatory polypeptide can contain a substitution of the amino acid at position 58 of SEQ ID NO:4. The purified variant costimulatory polypeptide can contain a substitution of the amino acid at position 69 of SEQ ID NO:4. The purified variant costimulatory polypeptide can contain a substitution of the amino acid at position 113 of SEQ ID NO:4. The wild-type polypeptide can be a B7-DC polypeptide [e.g., murine B7-DC (SEQ ID NO:6)]. The purified variant costimulatory polypeptide can contain a substitution of the amino acid at position 58 of SEQ ID NO:6.

In another aspect, the invention features an isolated nucleic acid molecule containing a nucleic acid sequence that encodes any of the variant costimulatory polypeptides provided herein. The invention also features a vector containing the nucleic acid. The nucleic acid sequence can be operably linked to an expression control sequence in the vector. In addition, the invention features a host cell containing the vector of the invention.

In another aspect, the invention features a method for enhancing T cell activation. The method can include contacting a T cell with any of the purified variant costimulatory polypeptides provided by the invention. The contacting can be in vitro. The T cell can be in a mammal. The method can include administering the variant polypeptide to the mammal. Alternatively, the method can involve administering a nucleic acid encoding the variant polypeptide to the mammal. The method can include administering a cell transfected or transduced with the nucleic acid to the mammal, wherein the cell is a cell, or a progeny of a cell, that prior to the transfection or the transduction, was obtained from the mammal. The mammal can be a human.

In yet another aspect, the invention features a polypeptide fragment of murine B7-H1 (SEQ ID NO:4), wherein the polypeptide fragment inhibits binding of murine B7-H1 to murine PD-1. The polypeptide fragment can contain, for example, amino acids 67-69, amino acids 113-115, or amino acids 124-126 of SEQ ID NO:4. The polypeptide fragment can also contain amino acids 62-69 of SEQ ID NO:4.

The invention also features a method of inhibiting the interaction between PD-1 and B7-H1. The method can include contacting a PD-1 polypeptide with a B7-H1 polypeptide fragment provided herein. The PD-1 can be in vitro or in a mammal. The method can involve administering the polypeptide fragment to the mammal, or the method can involve administering a nucleic acid encoding the polypeptide fragment to the mammal. The method can involve administering a cell transfected or transduced with the nucleic acid to the mammal, wherein the cell is a cell, or a progeny of a cell, that prior to the transfection or the transduction, was obtained from the mammal. The mammal can be a human.

In another aspect, the invention features a polypeptide fragment of murine B7-DC (SEQ ID NO:6), wherein the polypeptide inhibits binding of murine B7-DC to murine PD-1. The polypeptide fragment can contain, for example, amino acids 67-71, amino acids 101-105, or amino acids 111-113 of SEQ ID NO:6. The polypeptide fragment can also contain amino acids 101-113 of SEQ ID NO:6.

In another aspect, the invention features a method of inhibiting the interaction between PD-1 and B7-DC. The method can include contacting a PD-1 polypeptide with a B7-DC polypeptide fragment provided herein. The PD-1 can be in vitro or in a mammal. The method can involve administering the polypeptide fragment to the mammal. The method can involve administering a nucleic acid encoding the polypeptide fragment to the mammal. The method can involve administering a cell transfected or transduced with the nucleic acid to the mammal, wherein the cell is a cell, or a progeny of a cell, that prior to the transfection or the transduction, was obtained from the mammal. The mammal can be a human.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a depiction of the full-length, immature amino acid sequence of human B7-H1 (hB7-H1; SEQ ID NO:3).

FIG. 2 is a depiction of the full-length, immature amino acid sequence of mouse B7-H1 (mB7-H1; SEQ ID NO:4).

FIG. 3 is a depiction of the full-length, immature amino acid sequence of human B7-DC (hB7-DC; SEQ ID NO:5).

FIG. 4 is a depiction of the full-length, immature amino acid sequence of mouse B7-DC (mB7-DC; SEQ ID NO:6).

FIG. 5 is a depiction of a nucleotide sequence (SEQ ID NO:7) encoding a full-length, immature human B7-H1 polypeptide having the amino acid sequence shown in FIG. 1.

FIG. 6 is a depiction of a nucleotide sequence (SEQ ID NO:8) encoding a full-length, immature mouse B7-H1 polypeptide having the amino acid sequence shown in FIG. 2.

FIG. 7 is a depiction of a nucleotide sequence (SEQ ID NO:9) encoding a full-length, immature human B7-DC polypeptide having the amino acid sequence shown in FIG. 3.

FIG. 8 is a depiction of a nucleotide sequence (SEQ ID NO:10) encoding a full-length, immature mouse B7-DC polypeptide having the amino acid sequence shown in FIG. 4.

FIG. 9 is a structure-oriented sequence alignment of B7 molecules. The alignment includes sequences from the N-terminal IgV domains of human CD86 (hCD86), human CD80 (hCD80), human B7-H1 (hB7-H1), mouse B7-H1 (mB7-H1), human B7-H2 (hB7-H2), human B7-H3 (hB7-H3), human B7-DC (hPD-L2), and mouse B7-DC (mPD-L2) (SEQ ID NOs:11-18, respectively). β-strands observed in the x-ray structures of CD80 and CD86 are labeled (A'-G), and residue positions most conserved across the B7 family (e.g., large hydrophobic, charged/polar, or cysteine residues) are shaded. Potential N-linked glycosylation sites are boxed. CD86 residues shown in italics are involved in formation of the crystallographic homodimer interface, which is conserved in CD80, and residues shown in bold italics participate in CTLA-4 binding in the structure of the complex. Residue positions in mB7-H1 and mB7-DC that are most important for PD-1 binding, based on mutagenesis studies, are underlined and shown in bold type. Residues in mB7-H1 that, when mutagenized, demonstrated increased avidity for PD-1 are circled. Residue numbers indicate positions within mB7-H1 (upper numbers) and mB7-DC (lower numbers).

FIG. 10A shows results for binding of B7-H1Ig and B7-H1Ig mutants to immobilized PD-1Ig, while FIG. 10B shows results for binding of B7-DCIg and B7-DCIg mutants to immobilized PD-1Ig.

DETAILED DESCRIPTION

Figure 10A:
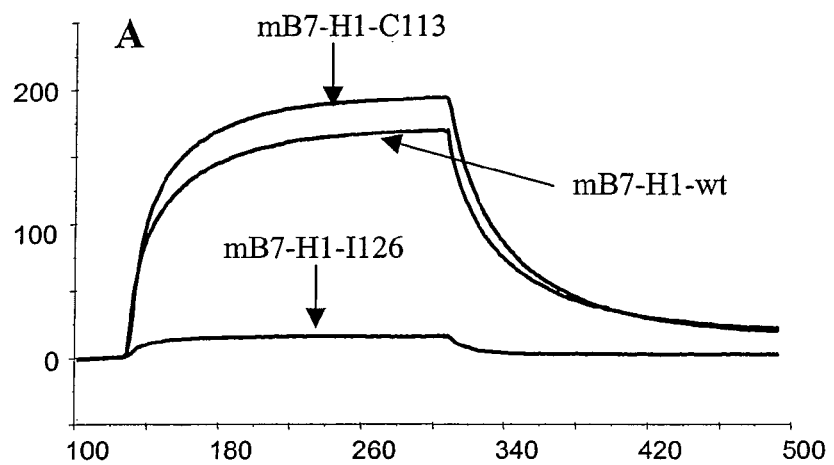
FIGS. 10A and 10B are line graphs showing results from surface plasmon resonance analysis of B7-H1 and B7-DC binding to PD-1.
Figure 10B:
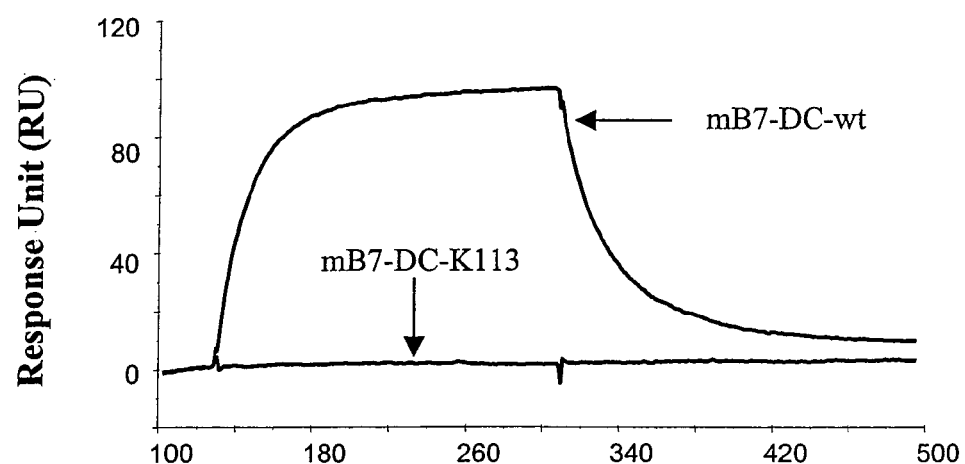

The invention provides materials and methods for enhancing a costimulatory response, enhancing T cell activation, and inhibiting interaction between a costimulatory molecule and PD-1. For example, the invention provides purified variant costimulatory polypeptides that have altered binding affinity for PD-1, but that retain substantial costimulatory activity. Since it is likely that the interaction of costimulatory molecules such as B7-H1 and B7-DC with PD-1 suppresses an immune response, variant B7-H1 and variant B7-DC polypeptides with decreased binding affinity for PD-1 can be useful to enhance an immune response.

1. Purified Polypeptides

Purified costimulatory polypeptides (e.g., purified B7-H1 and B7-DC polypeptides) are provided herein. As used herein, the term "polypeptide" refers to a chain of amino acids of any length, regardless of modification (e.g., phosphorylation or glycosylation). A "costimulatory polypeptide" is a polypeptide that, upon interaction with a cell-surface molecule on a T cell, enhances a T cell response (e.g., stimulates T cell proliferation and/or cytokine release). The T cell response that results from the interaction typically is greater than the response in the absence of the costimulatory polypeptide. The response of the T cell in the absence of the costimulatory polypeptide can be no response or can be a response significantly lower than in the presence of the costimulatory polypeptide. It is understood that the response of the T cell can be an effector (e.g., CTL or antibody-producing B cell) response, a helper response providing help for one or more effector (e.g., CTL or antibody-producing B cell) responses, or a suppressive response.

A costimulatory polypeptide can be a full-length costimulatory molecule, or can it be a portion (i.e., a functional fragment) of a costimulatory molecule. In some embodiments, a costimulatory polypeptide can be a variant of a full-length, immature B7-H1 polypeptide having the amino acid sequence shown in FIG. 1 or FIG. 2 (SEQ ID NO:3 and SEQ ID NO:4, respectively), or a variant of a full-length, immature B7-DC polypeptide having the amino acid sequence shown in FIG. 3 or FIG. 4 (SEQ ID NO:5 and SEQ ID NO:6, respectively). Alternatively, a costimulatory molecule of the invention can have, for example, a variant amino acid sequence from amino acid residue 20, 21, 22, 23, 24, 25, 26, 27, 28, 29, 30, 31, or 32 to (a) amino acid residue 290 of SEQ ID NO:3 or SEQ ID NO:4, (b) amino acid residue 273 of SEQ ID NO:5, or (c) amino acid residue 247 of SEQ ID NO:6. A costimulatory polypeptide that is a portion of a full-length costimulatory molecule typically has at least 20 percent (e.g., at least 20 percent, 30 percent, 40 percent, 50 percent, 60 percent, 70 percent, 80 percent, 90 percent, 95 percent, 98 percent, 99 percent, 100 percent, or even more than 100 percent) of the costimulatory activity of the full-length costimulatory molecule.

The costimulatory polypeptides provided herein can be variant polypeptides (e.g., variant B7-H1 or B7-DC polypeptides). As used herein, a "variant" costimulatory polypeptide contains at least one amino acid sequence alteration as compared to the amino acid sequence of the corresponding wild-type costimulatory polypeptide (e.g., a polypeptide having the amino acid sequence set forth in any of SEQ ID NOs:3-6). An amino acid sequence alteration can be, for example, a substitution, a deletion, or an insertion of one or more amino acids. With respect to SEQ ID NO:4, for example, a variant B7-H1 polypeptide can contain, without limitation, a substitution at position 67 (e.g., an alanine substitution for phenylalanine at position 67), a substitution at position 126 (e.g., an alanine substitution for isoleucine as position 126), a substitution at position 37 (e.g., a tyrosine substitution for threonine at position 37), a substitution at position 115 (e.g., an alanine substitution for isoleucine at position 115), or a substitution at position 124 (e.g., a serine substitution for lysine at position 124). With respect to SEQ ID NO:6, a variant B7-DC polypeptide can contain, without limitation, a substitution at position 111 (e.g., a serine substitution for aspartic acid at position 111), a substitution at position 113 (e.g., a serine substitution for lysine at position 113), a substitution at position 56 (e.g., a serine substitution for arginine at position 56), a substitution at position 67 (e.g., a tyrosine substitution for serine at position 67), a substitution at position 71 (e.g., a serine substitution for glutamic acid at position 71), a substitution at position 101 (e.g., a serine substitution for arginine at position 101), or a substitution at position 105 (e.g., an alanine substitution for isoleucine at position 105). It is understood, however, that the recited substitutions can be made using any amino acid or amino acid analog. For example, the substitutions at the recited positions can be made with any of the naturally-occurring amino acids (e.g., alanine, aspartic acid, asparagine, arginine, cysteine, glycine, glutamic acid, glutamine, histidine, leucine, valine, isoleucine, lysine, methionine, proline, threonine, serine, phenylalanine, tryptophan, or tyrosine).

While the substitutions described herein are with respect to mouse B7-H1 and mouse B7-DC, it is noted that one of ordinary skill in the art could readily make equivalent alterations in the corresponding polypeptides from other species (e.g., rat, hamster, guinea pig, gerbil, rabbit, dog, cat, horse, pig, sheep, cow, non-human primate, or human). For example, a variant human B7-H1 polypeptide can contain a substitution at position 67, 126, 37, or 124 with respect to the amino acid sequence set forth in SEQ ID NO:3, and a variant human B7-DC polypeptide can contain a substitution at position 111, 113, 67, 71, or 105 with respect to the amino acid sequence set forth in SEQ ID NO:5. Thus, the invention features variants of B7-H1 and B7-DC from all the above mammals, nucleic acids (e.g., DNA or RNA) encoding the variant B7-H1 and variant B7-DC polypeptides, vectors containing the nucleic acids, host cells containing the vectors, and methods of using the variants, the nucleic acids, and the host cells.

A variant costimulatory polypeptide of the invention can have reduced binding affinity for PD-1 as compared to the binding affinity of the corresponding wild-type costimulatory polypeptide. The binding affinity of a variant typically is reduced by at least 50 percent (e.g., at least 50 percent, 55 percent, 60 percent, 70 percent, 75 percent, 80 percent, 90 percent, 95 percent, 99 percent, or more than 99 percent) as compared to the binding affinity of the corresponding wild-type polypeptide. In addition, a variant costimulatory polypeptide with reduced binding affinity for PD-1 can retain substantial costimulatory activity. For example, a variant costimulatory polypeptide can have at least 20 percent (e.g., at least 20 percent, 25 percent, 30 percent, 40 percent, 50 percent, 60 percent, 75 percent, 90 percent, 100 percent, or more than 100 percent) of the level of costimulatory activity exhibited by the corresponding wild-type costimulatory polypeptide. Costimulatory activity can be measured by any of a number of methods, including those disclosed herein (e.g., T cell proliferation and cytokine assays).

The invention also provides polypeptides that are fragments of full-length costimulatory molecules (e.g., costimulatory molecules having the amino acid sequences set forth in SEQ ID NOs:3-6). Such polypeptide fragments typically contain a region of a costimulatory polypeptide that is important for binding affinity for PD-1. For example, a polypeptide fragment of mouse B7-H1 (SEQ ID NO:4) can contain amino acids 67-69, 113-115, or 124-126. A polypeptide fragment of mouse B7-DC can contain, for example, amino acids 67-71, 101-105, or 111-113. Without being bound by a particular mechanism, these fragments can be useful to inhibit the binding of a costimulatory polypeptide (e.g., a full-length, native costimulatory polypeptide) to PD-1 and consequent activation of T cell suppression. The binding to PD-1 typically is inhibited by at least 50 percent (e.g., at least 50 percent, 60 percent, 70 percent, 75 percent, 80 percent, 90 percent, 95 percent, or more than 95 percent) as compared to the level of binding in the absence of the fragment. In addition, such fragments can be useful to enhance an immune response, as inhibiting interactions of B7-H1 and B7-DC with PD-1 may also inhibit the suppression of immune responses that would otherwise occur.

Isolated costimulatory polypeptides of the invention can be obtained by, for example, chemical synthesis or by recombinant production in a host cell. To recombinantly produce a costimulatory polypeptide, a nucleic acid containing a nucleotide sequence encoding the polypeptide can be used to transform, transduce, or transfect a bacterial or eukaryotic host cell (e.g., an insect, yeast, or mammalian cell). In general, nucleic acid constructs include a regulatory sequence operably linked to a nucleotide sequence encoding a costimulatory polypeptide. Regulatory sequences (also referred to herein as expression control sequences) typically do not encode a gene product, but instead affect the expression of the nucleic acid sequences to which they are operably linked.

Useful bacterial systems include, for example, *Escherichia coli* strains such as BL-21. An *E. coli* strain can be transformed with a vector such as one of the pGEX series of vectors (Amersham Biosciences Corp., Piscataway, N.J.), which produce fusion proteins containing glutathione S-transferase (GST). Transformed *E. coli* typically are grown exponentially, and then stimulated with isopropylthiogalactopyranoside (IPTG) to induce expression of the polypeptide of interest. The expressed polypeptide may be soluble and easily purified from lysed cells by, for example, adsorption to glutathione-agarose beads followed by elution in the presence of free glutathione. The pGEX vectors are designed to include thrombin or factor Xa protease cleavage sites so that the target gene product can be released from the GST moiety.

In eukaryotic host cells, a number of viral-based expression systems can be utilized to express costimulatory polypeptides (e.g., variant B7-H1 and variant B7-DC polypeptides). A nucleic acid encoding a costimulatory polypeptide of the invention can be cloned into, for example, a baculoviral vector such as pBLUEBAC™ (Invitrogen Life Technologies, Carlsbad, Calif.), which can be used to co-transfect insect cells such as *Spodoptera frugiperda* (Sf9) cells with wild type DNA from *Autographa californica* multiply enveloped nuclear polyhedrosis virus (AcMNPV). Recombinant viruses producing costimulatory polypeptides can be identified by standard methodology. Alternatively, a nucleic acid encoding a costimulatory polypeptide such as variant B7-H1 or variant B7-DC can be introduced into an SV40, retroviral, or vaccinia based viral vector for infection of suitable host cells.

Mammalian cell lines that stably express variant costimulatory polypeptides can be produced using expression vectors with appropriate control elements and a selectable marker. For example, the eukaryotic expression vectors pCR®3.1 (Invitrogen Life Technologies) and p91023(B) (see Wong et al. (1985) *Science* 228:810-815) are suitable for expression of variant costimulatory polypeptides in, for example, Chinese hamster ovary (CHO) cells, COS-1 cells, human embryonic kidney 293 cells, NIH3T3 cells, BHK21 cells, MDCK cells, and human vascular endothelial cells (HUVEC). Following introduction of an expression vector by electroporation, lipofection, calcium phosphate, or calcium chloride co-precipitation, DEAE dextran, or other suitable transfection method, stable cell lines can be selected (e.g., by antibiotic resistance to G418, kanamycin, or hygromycin). The transfected cells can be cultured such that the polypeptide of interest is expressed, and the polypeptide can be recovered from, for example, the cell culture supernatant or from lysed cells. Alternatively, a variant costimulatory polypeptide can be produced by (a) ligating amplified sequences into a mammalian expression vector such as pcDNA™ 3 (Invitrogen Life Technologies), and (b) transcribing and translating in vitro using wheat germ extract or rabbit reticulocyte lysate.

Variant costimulatory polypeptides can be purified using, for example, chromatographic methods such as DEAE ion exchange, gel filtration, and hydroxylapatite chromatography. For example, a costimulatory polypeptide in a cell culture supernatant or a cytoplasmic extract can be purified using a protein G column. In some embodiments, variant costimulatory polypeptides can be "engineered" to contain an amino acid sequence that allows the polypeptides to be captured onto an affinity matrix. For example, a tag such as c-myc, hemagglutinin, polyhistidine, or FLAG™ (Kodak) can be used to aid polypeptide purification. Such tags can be inserted anywhere within the polypeptide, including at either the carboxyl or amino terminus. Other fusions that can be useful include enzymes that aid in the detection of the polypeptide, such as alkaline phosphatase. Immunoaffinity chromatography also can be used to purify costimulatory polypeptides.

2. Isolated Nucleic Acid Molecules

The invention provides isolated nucleic acids that include a nucleic acid sequence encoding a costimulatory polypeptide (e.g., a variant B7-H1 or B7-DC polypeptide). As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-B7-H1 or B7-DC proteins). The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule independent of other sequences (e.g., a chemically synthesized nucleic acid, or a cDNA or genomic DNA fragment produced by PCR or restriction endonuclease treatment), as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, a cDNA library or a genomic library, or a gel slice containing a genomic DNA restriction digest, is not to be considered an isolated nucleic acid.

Nucleic acids of the invention can be in sense or antisense orientation, or can be complementary to a reference sequence encoding a costimulatory polypeptide. Reference sequences include, for example, the nucleotide sequences set forth in SEQ ID NOS:7-10 (shown in FIGS. 5-8), which encode full-length, immature costimulatory polypeptides having the amino acid sequences set forth in SEQ ID NOS:3-6, respectively. Nucleic acids of the invention can be DNA, RNA, or nucleic acid analogs. Nucleic acid analogs can be modified at the base moiety, sugar moiety, or phosphate backbone. Such modification can improve, for example, stability, hybridization, or solubility of the nucleic acid. Modifications at the base moiety can include deoxyuridine for deoxythymidine, and 5-methyl-2'-deoxycytidine or 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone.

Isolated nucleic acid molecules of the invention can be produced by standard techniques, including, without limitation, common molecular cloning and chemical nucleic acid synthesis techniques. For example, polymerase chain reaction (PCR) techniques can be used to obtain an isolated nucleic acid encoding a variant costimulatory polypeptide. PCR is a technique in which target nucleic acids are enzymatically amplified. Typically, sequence information from the ends of the region of interest or beyond can be employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize a complementary DNA (cDNA) strand. Ligase chain reaction, strand displacement amplification, self-sustained sequence replication or nucleic acid sequence-based amplification also can be used to obtain isolated nucleic acids. See, for example, Lewis (1992) *Genetic Engineering News* 12:1; Guatelli et al. (1990) *Proc. Natl. Acad. Sci. USA* 87:1874-1878; and Weiss (1991) *Science* 254:1292-1293.

Isolated nucleic acids of the invention also can be chemically synthesized, either as a single nucleic acid molecule or as a series of oligonucleotides (e.g., using phosphoramidite technology for automated DNA synthesis in the 3' to 5' direction). For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase can be used to extend the oligonucleotides, resulting in a single, double-stranded nucleic acid molecule per oligonucleotide pair, which then can be ligated into a vector.

Isolated nucleic acids of the invention also can be obtained by mutagenesis. For example, a reference sequence (e.g., the nucleotide sequence set forth in SEQ ID NO:15, SEQ ID NO:16, SEQ ID NO:17, or SEQ ID NO:18) that encodes a costimulatory polypeptide having an amino acid sequence shown in FIGS. 1-4 (SEQ ID NOs:3-6) can be mutated using standard techniques, including oligonucleotide-directed mutagenesis and/or site-directed mutagenesis through PCR. See, *Short Protocols in Molecular Biology*, Chapter 8, Green Publishing Associates and John Wiley & Sons, edited by Ausubel et al., 1992. Examples of positions that can be modified include those described herein.

3. Vectors and Host Cells

The invention also provides vectors containing nucleic acids such as those described above. As used herein, a "vector" is a replicon, such as a plasmid, phage, or cosmid, into which another DNA segment may be inserted so as to bring about the replication of the inserted segment. The vectors of the invention can be expression vectors. An "expression vector" is a vector that includes one or more expression control sequences, and an "expression control sequence" is a DNA sequence that controls and regulates the transcription and/or translation of another DNA sequence.

In the expression vectors of the invention, the nucleic acid is operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses.

Numerous vectors and expression systems are commercially available from such corporations as Novagen (Madison, Wis.), Clontech (Palo Alto, Calif.), Stratagene (La Jolla, Calif.), and Invitrogen Life Technologies (Carlsbad, Calif.).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide including at either the carboxyl or amino terminus.

The invention also provides host cells containing vectors of the invention. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Suitable methods for transforming and transfecting host cells are found in Sambrook et al., *Molecular Cloning: A Laboratory Manual* (2$^{nd}$ edition), Cold Spring Harbor Laboratory, New York (1989), and reagents for transformation and/or transfection are commercially available [e.g., Lipofectin (Invitrogen Life Technologies); Fugene (Roche, Indianapolis, Ind.); and SuperFect (Qiagen, Valencia, Calif.)]. A host cell (e.g., a prokaryotic cell or a eukaryotic cell such as a COS cell) can be used to, for example, produce the costimulatory polypeptides provided herein. In some embodiments, a host cell (e.g., an APC) can be used to express the costimulatory polypeptides of the invention for presentation to a T cell.

4. Methods

The invention provides methods that include using variant costimulatory polypeptides to enhance T cell responses. The costimulatory molecules B7-H1 and B7-DC can bind to PD-1 (programmed cell death-1), a CD28 homolog with an immunoreceptor tyrosine-based inhibitory motif in its cytoplasmic domain (Ishida et al. (1992) *EMBO J.* 11:3887-3895). PD-1 is expressed on a subset of thymocytes and is up-regulated on T cells, B cells, and myeloid cells after their activation (Agata et al. (1996) *Int. Immunol.* 8:765-772).

PD-1 appears to be a negative regulator of immune responses in vivo. For example, PD-1$^{-/-}$ mice in the C57BL/6 background slowly developed a lupus-like glomerulonephritis and progressive arthritis (Nishimura et al. (1999) *Immunity* 11:141-151). Additionally, PD-1$^{-/-}$ mice in the BALB/c background rapidly developed a fatal autoimmune dilated cardiomyopathy (Nishimura et al. (2001) *Science* 291:319-322). Evidence also indicates, however, that both B7-H1 and B7-DC can function to costimulate a T cell response. In the presence of suboptimal TCR signals, B7-H1 or B7-DC can stimulate increased proliferation and production of cytokines in vitro. In addition, infusion of a B7-H1Ig fusion polypeptide can increase CD4$^+$ T cell responses and Th-dependent humoral immunity. Thus, B7-H1 and B7-DC may also bind to T cell receptors other than PD-1. Indeed, it has been shown that B7-H1 expressed on tumor cells can actively inhibit immune responses by promoting the apoptosis of effector CTLs, and the apoptotic effect of B7-H1 is mediated largely by receptors other than PD-1 (Dong et al. (2002) *Nature Med.* 8:793-800).

The experiments described in the Examples below indicate that the costimulatory activity of B7-H1 and B7-DC, and the described variants of each, is not mediated by the PD-1 receptor. Thus, the invention provides methods for using a variant costimulatory polypeptide with reduced affinity for PD-1 to stimulate a T cell response. The methods can include contacting a T cell with a purified variant costimulatory polypeptide. The contacting can be in vitro, ex vivo, or in vivo (e.g., in a mammal such as a mouse, rat, rabbit, dog, cow, pig, non-human primate, or a human).

The contacting can occur before, during, or after activation of the T cell. Typically, contacting of the T cell with variant costimulatory polypeptide can be at substantially the same time as activation. Activation can be, for example, by exposing the T cell to an antibody that binds to the T cell receptor (TCR) or one of the polypeptides of the CD3 complex that is physically associated with the TCR. Alternatively, a T cell can be exposed to either an alloantigen (e.g., a MHC alloantigen) on, for example, an APC [e.g., an interdigitating dendritic cell (referred to herein as a dendritic cell), a macrophage, a monocyte, or a B cell] or an antigenic peptide produced by processing of a protein antigen by any of the above APC and presented to the T cell by MHC molecules on the surface of the APC. The T cell can be a $CD4^+$ T cell or a $CD8^+$ T cell.

In some embodiments, a purified variant costimulatory polypeptide can be administered directly to a T cell. Alternatively, an APC such as a macrophage, monocyte, interdigitating dendritic cell (referred to herein as a dendritic cell), or B cell can be transformed, transduced, or transfected with a nucleic acid containing a nucleotide sequence that encodes a variant costimulatory polypeptide, and the T cell can be contacted by the transformed, transduced, or transfected APC. The transformed, transduced, or transfected cell can be a cell, or a progeny of a cell that, prior to being transformed, transduced, or transfected, was obtained from the subject to which it is administered, or from another subject (e.g., another subject of the same species).

The variant costimulatory polypeptide can be any of those described herein. For example, a B7-H1 polypeptide can contain a substitution at position 67, position 126, position 37, position 115, or position 124 (e.g., an alanine substitution for phenylalanine at position 67, an alanine substitution for isoleucine as position 126, a tyrosine substitution for threonine at position 37, an alanine substitution for isoleucine at position 115, or a serine substitution for lysine at position 124), each with respect to SEQ ID NO:4. Alternatively, the variant costimulatory polypeptide can be, for example, a B7-DC polypeptide containing a substitution at position 111, 113, 56, 67, 71, 101, or 105 (e.g., a serine substitution for aspartic acid at position 111, a serine substitution for lysine at position 113, a serine substitution for arginine at position 56, a tyrosine substitution for serine at position 67, a serine substitution for glutamic acid at position 71, a serine substitution for arginine at position 101, or an alanine substitution for isoleucine at position 105), each with respect to SEQ ID NO:6.

If the activation is in vitro, the variant B7-H1 molecule or variant B7-DC molecule can be bound to the floor of a the relevant culture vessel, e.g. a well of a plastic microtiter plate.

In vitro application of the purified variant costimulatory polypeptides can be useful, for example, in basic scientific studies of immune mechanisms or for production of activated T cells for use in studies of T cell function or, for example, passive immunotherapy. Furthermore, variant B7-H1 and variant B7-DC polypeptides can be added to in vitro assays (e.g., T cell proliferation assays) designed to test for immunity to an antigen of interest in a subject from which the T cells were obtained. Addition of variant costimulatory polypeptides to such assays would be expected to result in a more potent, and therefore more readily detectable, in vitro response. Moreover, a variant B7-H1 or B7-DC polypeptide, or an APC transformed, transfected, or transduced with a nucleic acid encoding such a polypeptide, can be used: (a) as a positive control in an assay to test for co-stimulatory activity in other molecules; or (b) in screening assays for compounds useful in inhibiting T costimulation (e.g., compounds potentially useful for treating autoimmune diseases or organ graft rejection).

The variant B7-H1 and variant B7-DC polypeptides provided herein are generally useful as in vivo and ex vivo as immune response-stimulating therapeutics. For example, the polypeptides of the invention can be used for treatment of disease conditions characterized by immunosuppression, such as, without limitation, cancer, AIDS or AIDS-related complex, other virally or environmentally-induced conditions, and certain congenital immune deficiencies. The polypeptides also can be employed to increase immune function that has been impaired by the use of radiotherapy of immunosuppressive drugs (e.g., certain chemotherapeutic agents), and therefore can be particularly useful when given in conjunction with such drugs or radiotherapy. In addition, variant B7-H1 molecules can be used to treat conditions involving cellular immune responses, including, for example, inflammatory conditions (e.g., conditions induced by infectious agents such as *Mycobacterium tuberculosis* or *M. leprae*), or other pathologic cell-mediated responses such as those involved in autoimmune diseases (e.g., rheumatoid arthritis, multiple sclerosis, or insulin-dependent diabetes mellitus).

Methods of the invention can be applied to a wide range of species, e.g., humans, non-human primates, horses, cattle, pigs, sheep, goats, dogs, cats, rabbits, guinea pigs, hamsters, rats, and mice.

In some in vivo approaches, a variant B7-H1 or variant B7-DC polypeptide (or a functional fragment thereof) itself is administered to a subject in a therapeutically effective amount. Typically, polypeptides of the invention can be suspended in a pharmaceutically-acceptable carrier. Pharmaceutically acceptable carriers are biologically compatible vehicles (e.g., physiological saline) that are suitable for administration to a human. A therapeutically effective amount is an amount of a variant costimulatory polypeptide that is capable of producing a medically desirable result (e.g., an enhanced T cell response) in a treated animal. Variant costimulatory polypeptides can be administered orally or by intravenous infusion, or injected subcutaneously, intramuscularly, intraperitoneally, intrarectally, intravaginally, intranasally, intragastrically, intratracheally, or intrapulmonarily.

The variant costimulatory polypeptides can be delivered directly to an appropriate lymphoid tissue (e.g., spleen, lymph node, or mucosal-associated lymphoid tissue). The dosage required typically depends on the choice of the route of administration, the nature of the formulation, the nature of the subject's illness, the subject's size, weight, surface area, age, and sex, other drugs being administered, and the judgment of the attending physician. Suitable dosages typically are in the range of 0.01-100.0 µg/kg. Wide variations in the needed dosage are to be expected in view of the variety of polypeptides and fragments available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2- or 3-, 4-, 6-, 8-, 10-, 20-, 50-, 100-, 150-, or more fold). Encapsulation of a purified variant costimulatory polypeptide in a suitable delivery vehicle (e.g., polymeric microparticles or implantable devices) may increase the efficiency of delivery, particularly for oral delivery.

Alternatively, a nucleic acid containing a nucleotide sequence encoding a variant B7-H1 or B7-DC polypeptide or functional fragment thereof can be delivered to an appropriate cell of an animal. Expression of the coding sequence typically is directed to lymphoid tissue of the subject by, for example, delivery of the nucleic acid to the lymphoid tissue. This can be achieved by, for example, using a polymeric, biodegradable microparticle or microcapsule delivery vehicle, sized to optimize phagocytosis by phagocytic cells such as macrophages. For example, PLGA (poly-lacto-co-glycolide) microparticles approximately 1-10 µm in diameter can be used. The nucleic acid can be encapsulated in these microparticles, which are taken up by macrophages and gradually biodegraded within the cell, thereby releasing the nucleic acid. Once released, the nucleic acid can be expressed within the cell. A second type of microparticle that also can be useful is intended not to be taken up directly by cells, but rather to serve primarily as a slow-release reservoir of nucleic acid. The nucleic acid is taken up by cells only upon release from the microparticle through biodegradation. Such polymeric particles typically are large enough to preclude phagocytosis (i.e., larger than 5 µm, and typically larger than 20 µm).

Another way to achieve uptake of a nucleic acid is to use liposomes, which can be prepared by standard methods known in the art, for example. Nucleic acid vectors can be incorporated alone into these delivery vehicles or can be co-incorporated with tissue-specific antibodies. Alternatively, a molecular conjugate can be prepared to contain a plasmid or other vector attached to poly-L-lysine by electrostatic or covalent forces. Poly-L-lysine binds to a ligand that can bind to a receptor on target cells (Cristiano et al. (1995) *J. Mol. Med.* 73:479-486). Alternatively, lymphoid tissue specific targeting can be achieved using lymphoid tissue-specific transcriptional regulatory elements (TREs) such as a B lymphocyte-, T lymphocyte-, or dendritic cell-specific TRE. Lymphoid tissue specific TREs include, for example, those known in the art [see, e.g., Thompson et al. (1992) *Mol. Cell. Biol.* 12:1043-1053; Todd et al. (1993) *J. Exp. Med.* 177: 1663-1674; and Penix et al. (1993) *J. Exp. Med.* 178:1483-1496]. Delivery of "naked DNA" (i.e., without a delivery vehicle) to an intramuscular, intradermal, or subcutaneous site is another means to achieve in vivo expression.

For in vivo expression of the variant costimulatory polypeptides provided herein, short amino acid sequences can act as signals to direct the polypeptides to specific intracellular compartments. For example, hydrophobic signal peptides having amino acid sequences such as MAISGVPVLGFFIIAVLMSAQESWA (SEQ ID NO:19) are found at the amino terminus of proteins destined for the ER. In addition, amino acid sequences such as KFERQ (SEQ ID NO:20) and other closely related sequences can target intracellular polypeptides to lysosomes, while amino acid sequences such as, for example, MDDQRDLISNNEQLP (SEQ ID NO:21) can direct polypeptides to endosomes. In addition, the amino acid sequence KDEL (SEQ ID NO:22) can act as a retention signal for the ER. Each of these signal peptides, or a combination thereof, can be used to traffic the variant B7-H1 and variant B7-DC polypeptides of the invention to specific cellular compartments. DNAs encoding the variant B7-H1 and B7-DC polypeptides containing targeting signals can be generated by, for example, PCR or other standard genetic engineering or synthetic techniques.

Similar to polypeptides, a therapeutic amount of a nucleic acid can be administered in a pharmaceutically acceptable carrier such as, for example, physiological saline. A therapeutically effective amount of a nucleic acid is an amount of the nucleic acid that is capable of producing a medically desirable result (e.g., an enhanced T cell response) in a treated animal. As described above, dosages will vary. Typical dosages for administration of nucleic acids are from approximately $10^6$ to $10^{12}$ copies of the nucleic acid molecule. This dose can be repeatedly administered, as needed. Routes of administration can be any of those listed above.

Ex vivo methods can include, for example, the steps of harvesting cells from a subject, culturing the cells, transducing them with an expression vector, and maintaining the cells under conditions suitable for expression of the variant costimulatory polypeptides provided herein. These methods are known in the art of molecular biology. The transduction step can be accomplished by any standard means used for ex vivo gene therapy, including, for example, calcium phosphate, lipofection, electroporation, viral infection, and biolistic gene transfer. Alternatively, liposomes or polymeric microparticles can be used. Cells that have been successfully transduced then can be selected, for example, for expression of the coding sequence or of a drug resistance gene. The cells then can be lethally irradiated (if desired) and injected or implanted into the subject.

In some ex vivo methods, peripheral blood mononuclear cells (PBMC) can be withdrawn from a patient or a suitable donor and exposed ex vivo to an activating stimulus (see above) and a variant costimulatory polypeptide (whether in soluble form or attached to a sold support by standard methodologies). The PBMC containing highly activated T cells then can be introduced into the same or a different patient.

An alternative ex vivo strategy can involve transfecting or transducing cells obtained from a subject with a nucleic acid encoding a variant B7-H1 or B7-DC polypeptide. The transfected or transduced cells then can be returned to the subject. While such cells typically would be hemopoietic cells (e.g., bone marrow cells, macrophages, monocytes, dendritic cells, or B cells), they can also be any of a wide range of types including, without limitation, fibroblasts, epithelial cells, endothelial cells, keratinocytes, or muscle cells in which they act as a source of the variant B7-H1 or B7-DC polypeptide for as long as they survive in the subject. The use of hemopoietic cells, including the above APC, can be particularly useful, as such cells typically are expected to home to, among others, lymphoid tissue (e.g., lymph nodes or spleen) and thus the variant B7-H1 or B7-DC polypeptide can be produced in high concentration at the site where its effect (i.e., enhancement of an immune response) is exerted. In addition, if APC are used, the APC expressing the exogenous variant costimulatory molecule can be the same APC that present an alloantigen or antigenic peptide to the relevant T cell. The variant B7-H1 or variant B7-DC can be secreted by the APC or expressed on its surface.

Methods for inhibiting interactions of B7-H1 or B7-DC with PD-1 also are provided herein. These methods can include contacting a PD-1 polypeptide with a fragment of B7-H1 or B7-DC. The fragment can contain, for example, amino acids 67-69 of B7-H1, amino acids 113-115 of B7-H1, or amino acids 124-126 of B7-H1, each with respect to SEQ ID NO:4. Alternatively, the fragment can contain, for example, amino acids 67-71 of B7-DC, amino acids 101-105 of B7-DC, or amino acids 111-113 of B7-DC, each with respect to SEQ ID NO:6.

The PD-1 polypeptide can be contacted in vitro or in vivo (e.g., in a mammal such as a mouse, rat, rabbit, dog, cow, non-human primate, or human). The polypeptide fragment can be administered directly, or the method can include administering to a mammal a nucleic acid containing a nucleotide sequence encoding the polypeptide fragment. In some embodiments, the method can include administering to a mammal a cell, or the progeny of a cell, that has been transformed, transduced, or transfected with a nucleic acid encoding the polypeptide fragment. The cell can be a cell, or a progeny of a cell that, prior to being transformed, transduced, or transfected, was obtained from the mammal to which the cell is administered.

5. Articles of Manufacture

The invention also provides articles of manufacture that can contain the variant costimulatory polypeptides, functional fragments of costimulatory polypeptides, and/or inhibitory fragments of costimulatory polypeptides provided herein. Articles of manufacture also can include the nucleic acids and host cells provided herein. For example, an article of manufacture can include a variant B7-H1 or B7-DC polypeptide, or a nucleic acid encoding a variant B7-H1 or variant B7-DC polypeptide, packaged in a container (e.g., a vial). In addition, such an article of manufacture can include a label or instructions indicating that the polypeptide or nucleic acid can be used to enhance T cell activation. Alternatively, an article of manufacture can include a fragment of a B7-H1 or B7-DC polypeptide packaged in a container, and also can include a label or instructions indicating that the fragment can be used to inhibit binding to PD-1.

The invention will be further described in the following examples, which do not limit the scope of the invention described in the claims.

EXAMPLES

Example 1

Materials and Methods

Mice and Cell lines: Female C57BL/6 (B6) mice were purchased from the National Cancer Institute (Frederick, Md.). PD-1-deficient (PD-1$^{-/-}$) mice were generated as described previously (Nishimura et al. (1998) *Int. Immunol.* 10:1563-1572). Stably transfected Chinese hamster ovary (CHO) cell clones secreting fusion proteins were maintained in CHO-SF II medium (Invitrogen Life Technologies) supplemented with 1% dialyzed fetal bovine serum (FBS; HyClone, Logan, Utah). Lymphocytes and COS cells were grown in Dulbecco's modified Eagle medium (DMEM; Invitrogen Life Technologies) supplemented with 10% FBS, 25 mM HEPES, 2 mM L-glutamine, 1 mM sodium pyruvate, 1% MEM nonessential amino acids, 100 U/ml penicillin G, and 100 μg/ml streptomycin sulfate.

Ig Fusion Proteins: Fusion proteins containing the extracellular domain of mouse PD-1 linked to the Fc portion of mouse IgG2a (PD-1Ig) were produced in stably transfected CHO cells and purified by protein G affinity column as described previously (Wand et al. supra). Total RNA was isolated from mouse spleen cells and B7-DC cDNA was obtained by reverse-transcription PCR. B7-H1Ig and B7-DCIg were prepared by transiently transfecting COS cells with a plasmid containing a chimeric cDNA that included the extracellular domain of mouse B7-H1 (Tamura et al. supra) or B7-DC linked in frame to the CH2-CH3 portion of human IgG1. The transfected COS cells were cultured in serum-free DMEM, and concentrated supernatants were used as sources of Ig fusion proteins for initial binding assays. The Ig proteins were further purified on a protein G column for BIAcore analysis and functional assays as described previously (Wand et al. supra).

Molecular modeling: Molecular models of the Ig V-type domains of human B7-H1 (hB7-H1), mouse B7-H1 (mB7-H1), human B7-DC (hB7-DC), and mouse B7-DC (mB7-DC) were generated by homology (or comparative) modeling based on X-ray coordinates of human CD80 and CD86, as seen in the structures of the CD80/CTLA-4 and CD86/CTLA-4 complexes. First, the V-domains of CD80 and CD86 were optimally superimposed, and sequences of B7 family members were aligned based on this superimposition. The superimposition and initial alignments were carried out using the sequence-structure alignment function of MOE (Molecular Operating Environment, Chemical Computing Group, Montreal, Quebec, Canada). The alignment was then manually adjusted to match Ig consensus positions and to map other conserved hydrophobic residues in the target sequences to core positions in the X-ray structures. Corresponding residues in the aligned sequences thus were predicted to have roughly equivalent spatial positions. Taking this kind of structural information into account typically is a more reliable alignment criterion than sequence identity alone if the identity is low, as in this case. In the aligned region, the average identity of the compared B7 sequences relative to the two structural templates, CD80 and CD86, was only approximately 16%. The final version of the structure-oriented sequence alignment, which provided the basis for model building, is shown in FIG. 9. Following the alignment, core regions of the four models were automatically assembled with MOE from the structural templates, and insertions and deletions in loop regions were modeled by applying a segment matching procedure (Levitt (1992) *J. Mol. Biol.* 226: 507-533; and Fechteler et al. (1995) *J. Mol. Biol.* 253:114-131). Side chain replacements were carried out using preferred rotamer conformations seen in high-resolution protein databank structures (Ponder and Richards (1987) *J. Mol. Biol.* 193:775-791; and Berman et al. (2000) *Nucl. Acids Res.* 28:235-242). In each case, twenty intermediate models were generated, average coordinates were calculated, and the resulting structures were energy minimized using a protein force field (Engh and Huber (1991) *Acta Cryst.* A47:392-400) until intramolecular contacts and stereochemistry of each model were reasonable. Graphical analysis of the models, including calculation of solvent-accessible surfaces (Connolly (1983) *J. Appl. Cryst.* 16:548-558) and residue mapping studies were carried out with INSIGHTII® (Accelrys, San Diego, Calif.).

Site-directed Mutagenesis: All mutants of B7-H1Ig and B7-DCIg were constructed using a two-step PCR technique, in which B7-H1Ig and B7-DCIg cDNAs, respectively, were used as templates. Overlapping oligonucleotide primers were synthesized to encode the desired mutations, and two flanking 5' and 3' primers were designed to contain EcoR I and Bgl II restriction sites, respectively. Appropriate regions of the cDNAs initially were amplified using the corresponding overlapping and flanking primers. Using the flanking 5' and 3' primers, fragments with overlapping sequences were fused together and amplified. PCR products were digested with EcoR I and Bgl II and ligated into EcoR I/Bgl II-digested pHIg vectors. To verify that the desired mutations were introduced, each mutant was sequenced using an ABI Prism 310 Genetic Analyzer. Plasmids were transfected into COS cells, and serum-free supernatants were harvested and used for in vitro binding assays or purified on a protein G column for BIAcore analysis and functional assays.

ELISA: A sandwich ELISA specific for B7-H1Ig and B7-DCIg was established as described previously. Briefly, microtiter plates were coated with 2 µg/ml goat anti-human IgG (Sigma, St. Louis, Mo.) overnight at 4° C. Wells were blocked for 1 hour with blocking buffer (10% FBS in PBS) and washed with PBS containing 0.05% Tween 20 (PBS-Tween). COS cell culture supernatants were added and incubated for 2 hours at room temperature. Known concentrations of purified B7-H1Ig also were added to separate wells on each plate for generation of a standard curve. After extensive washing, horseradish peroxidase (HRP)-conjugated goat anti-human IgG (TAGO, Inc., Burlingame, Calif.) diluted 1:2000 was added and subsequently developed with TMB substrate before stopping the reaction by the addition of 0.5 M $H_2SO_4$. Absorbance was measured at 405 nm on a microtiter plate reader. Concentrations of mutant fusion proteins were determined by comparison with the linear range of a standard curve of B7-H1Ig. Data from triplicate wells were collected, and the standard deviations from the mean were <10%. Experiments were repeated at least three times.

The ability of mutant and wild type B7-H1Ig and B7-DCIg fusion polypeptides to bind PD-1 was measured using a capture ELISA assay. Recombinant PD-1Ig fusion proteins were coated on microtiter plates at 5 µg/ml overnight at 4° C. The plates were blocked and washed, and COS cell culture media was added and incubated for 2 hours at room temperature. After extensive washing, HRP-conjugated goat anti-human IgG was added, followed by TMB substrate and measurement of absorbance at 405 nm.

Flow Cytometry: Human embryonal kidney 293 cells were transfected with a PD-1GFP vector, which was constructed by fusing GFP (green fluorescent protein cDNA) in frame to the C terminal end of a full-length mouse PD-1 cDNA. The cells were harvested 24 hours after transfection and incubated in FACS (fluorescence activated cell sorting) buffer (PBS, 3% FBS, 0.02% $NaN_3$) with equal amounts of fusion proteins, which had been titrated using wild type B7-H1Ig and B7-DCIg, in COS cell culture media on ice for 45 minutes. An unrelated fusion protein containing human Ig was used as a negative control. The cells were washed, further incubated with fluorescein isothiocyanate (PE)-conjugated goat anti-human IgG (BioSource, Camarillo, Calif.), and analyzed on a FACScaliber (Becton Dickinson, Mountain View, Calif.) with Cell Quest software (Becton Dickinson). GFP-positive cells were gated by FL1.

Surface Plasmon Resonance Analysis: The affinity of purified wild type and mutant B7-H1 and B7-DC polypeptides was analyzed on a BIACORE™ 3000 instrument (Biacore AB, Uppsala, Sweden). All reagents except fusion proteins were purchased, pre-filtered, and degassed from BIAcore. All experiments were performed at 25° C. using 0.1 M HEPES, 0.15 M NaCl (pH 7.4) as a running buffer. Briefly, PD-1Ig was first immobilized onto a CM5 sensor chip (BIAcore) by amine coupling according to the BIAcore protocol. A flow cell of the CM5 chip was derivatized through injection of a 1:1 EDC:NHS [N-ethyl-N'-(diethylaminopropyl) carbodiimide:N-hydroxysuccinimide] mixture for seven minutes, followed by injection of 20 µg/ml of PD-1Ig at 10 µl/min diluted in 10 mM sodium acetate (pH 4.5). The PD-1Ig was immobilized at 2000 RUs. This was followed by blocking the remaining activated carboxyl groups with 1 M ethanolamine (pH 8.5). A control flow cell was prepared in a similar fashion as above, substituting running buffer alone in place of PD-1Ig. The fusion proteins were diluted in running buffer in a concentration series of 3.75, 7.5, 15, 30, and 60 µg/ml. The proteins were injected at a flow rate of 20 µl/min for 3 minutes, and buffer was allowed to flow over the surface for 5 minutes for dissociation data. The flow cells were regenerated with a single 30-second pulse of 10 mM NaOH. Data analysis was performed using BIAevaluation software package 3.1 (BIAcore).

T cell proliferation and cytokine assays: T cells from wild type B6 mice or PD-1$^{-/-}$ mice were purified using nylon wool columns (Robbins Scientific Co, Sunnyvale, Calif.) as described previously (Wang et al. supra). The enriched T cells were cultured at $3\times10^5$ cells per well in flat-bottomed 96-well microplates that were pre-coated with anti-CD3 mAb (clone 145-2C11, Pharmingen, San Diego, Calif.) in the presence of 5 µg/ml of fusion or control polypeptides. Proliferation of T cells was determined by incorporation of 1 µCi/well $^3$H-TdR during the last 12 hours of the 3-day culture. $^3$H-TdR incorporation was counted using a MICROBETA® Trilux liquid scintillation counter (Wallac, Finland). To detect cytokine, culture supernatants were collected at various time points, and the concentration of IFN-γ was measured by sandwich ELISA following the manufacturer's instructions (Pharmingen).

Example 2

Sequences, Structures, and Molecular Models

The V-regions in CD80 and CD86 share only limited sequence identity (approximately 20%), but their three-dimensional structures are very similar as revealed by independent crystallographic studies. Many core or Ig superfamily consensus residue positions seen in CD80/CD86 also are conserved or conservatively replaced in other B7 family members, including B7-H1 and B7-DC (FIG. 9).

Molecular models of mouse and human B7-H1 and B7-DC molecules were constructed. These models revealed that in the V-regions, B7-H1 and B7-DC share more sequence identity than average across the B7 family—approximately 34%. Since both B7-H1 and B7-DC bind PD-1, residue conservation could be significant for formation of the receptor binding structure. Therefore, the models were used to compare the putative distribution of conserved residues that are exposed on the protein surface. A side-by-side comparison of these molecular models revealed significant conservation of surface residues on the BED faces of B7-H1 and B7-DC, more so in the human than the mouse proteins. In contrast, the opposite A'GFCC'C" faces did not display significant residue conservation. This result was somewhat unexpected because the corresponding A'GFCC'C" faces of both CD80 and CD86 contain the CD28/CTLA-4 binding sites.

Example 3

Mutagenesis Analysis of Receptor Binding Sites

With the aid of the molecular models, the V-domains of B7-H1 and B7-DC were scanned for important residues. Conserved and non-conserved residues on both the BED and A'GFCC'C" faces were selected for site-specific mutagenesis. Residues in the mouse molecules were mutated to enable subsequent functional studies of selected mutant proteins. The binding characteristics of the resulting mutant proteins were assessed by specific ELISA and FACS analysis for binding to PD-1. A total of 21 mB7-H1 and 17 mB7-DC mutants were prepared and tested. The results are summarized in Tables 1 and 2. Particular residues within mB7-H1 and mB7-DC were only considered to be important for ligand-receptor interactions if their mutation caused at least a 50% loss of binding by FACS, or at least an order of magnitude loss by ELISA.

Mutation of about half of these residues significantly abolished binding to mPD-1. In particular, mB7-H1 residues F67, I115, K124, and I126 were identified as important for binding to mPD1. For mB7-DC, the identified residues were E71, I105, D111, and K113. All of these important residues are located in the C', C", F, and G strands of the A'GFCC'C" face, but not in the BED face. Mutation of three residues in mB7-H1 (E58, A69, and C113) increased binding to mPD-1 three- to four-fold as determined by ELISA. Thus, these positions must at least be proximal to the receptor-ligand interface and have not only some tolerance for substitution but also potential optimization of binding interactions.

TABLE 1

Summary of amino acid substitutions and binding characteristics of mouse B7-H1 mutants

| | | Substitutions[b] | | Binding activity | |
|---|---|---|---|---|---|
| Mutants[a] | Sites | Nucleic acid | Amino acid | FACS | ELISA (%)[c] |
| B7-H1 | | | | ++++ | 100 |
| L27A | A' strand | TTG > GCC | Leu > Ala | ++++ | 100 |
| E31S | A' strand | GAG > AGC | Glu > Ser | ++ | 50 |
| S34Y | B strand | AGC > TAC | Ser > Tyr | ++++ | 60 |
| T37Y | B strand | ACG > TAC | Thr > Tyr | ++ | 5 |
| D49S | B/C strand | GAC > AGC | Asp > Ser | ++++ | 30 |
| Y56S | C strand | TAC > AGC | Tyr > Ser | ++++ | 100 |
| E58S | C strand | GAA > AGC | Glu > Ser | +++++ | 300 |
| E62S | C/C' strand | GAG > AGC | Glu > Ser | ++++ | 50 |
| F67A | C' strand | TTT > GCC | Phe > Ala | +/− | 2 |
| A69F | C' strand | GCA > TTC | Ala > Phe | +++++ | 300 |
| E72S | C' strand | GAG > AGC | Glu > Ser | ++++ | 60 |
| K75S | C"/D strand | AAG > AGC | Lys > Ser | ++++ | 100 |
| K89S | D strand | AAG > AGC | Lys > Ser | ++++ | 60 |
| A98F | E strand | GCC > TTC | Ala > Phe | ++++ | 40 |
| Q100S | E strand | CAG > AGC | Gln > Ser | ++++ | 100 |
| C113Y | F strand | TGC > TAC | Cys > Tyr | +++++ | 300 |
| I115A | F strand | ATA > GCC | Ile > Ala | +/− | 3 |
| S117Y | F strand | AGC > TAC | Ser > Tyr | ++++ | 100 |
| K124S | G strand | AAG > AGC | Lys > Ser | + | 3 |
| I126A | G strand | ATC > GCC | Ile > Ala | − | 1.4 |
| K129S | G strand | AAA > AGC | Lys > Ser | ++ | 35 |

[a]Amino acids are numbered from the initiator methionine.

[b]Nucleotides or amino acids in front of the slash were replaced with the corresponding nucleotides or amino acids after the slash.

[c]Specific binding activities were determined for each of the indicated fusion proteins. The concentration of a fusion protein required to give an arbitrary $A_{405}$ the same as that found for wild type B7-H1Ig was determined from the linear region of binding curves and expressed as a percentage of specific binding activity of B7-H1Ig. Values represent the average of three determinations from each binding curve, and are representative of four experiments.

TABLE 2

Summary of amino acid substitutions and binding characteristics of mouse B7-DC mutants

| | | Substitutions[b] | | Binding activity | |
|---|---|---|---|---|---|
| Mutants[a] | Sites | Nucleic acid | Amino acid | FACS | ELISA (%)[c] |
| B7-DC | | | | ++++ | 100 |
| D33S | A' strand | GAC > AGC | Asp > Ser | ++++ | 30 |
| S39Y | B strand | AGC > TAC | Ser > Tyr | ++++ | 60 |
| E41S | B strand | GAG > AGC | Glu > Ser | ++++ | 100 |
| R56S | C strand | AGA > TCT | Arg > Ser | +++/++ | 5 |
| S58Y | C strand | AGT > TAC | Ser > Tyr | ++++ | 170 |
| D65S | C' strand | GAT > AGC | Asp > Ser | ++++ | 100 |
| S67Y | C' strand | TCT > TAC | Ser > Tyr | +++/++ | 3 |
| E71S | C" strand | GAA > AGC | Glu > Ser | +++/++ | 2 |
| R72S | C" strand | AGA > AGC | Arg > Ser | ++++ | 60 |
| K84S | D strand | AAG > AGC | Lys > Ser | +++/++++ | 13 |
| H88A | E strand | CAC > GCC | His > Ala | +++/++++ | 20 |
| R101S | F strand | CGT > AGC | Arg > Ser | +++ | 7 |
| L103A | F strand | CTG > GCC | Leu > Ala | +++ | 25 |
| 1105A | F strand | ATC > GCC | Ile > Ala | ++ | 0.5 |
| D111S | G strand | GAC > AGC | Glu > Ser | ++ | 0.3 |
| K113S | G strand | AAG > AGC | Lys > Ser | +/− | <0.1 |
| T116Y | G strand | ACG > TAC | Thr > Tyr | +++/++++ | 20 |

[a]Amino acids are numbered from the initiation methionine.

[b]The nucleotides or amino acids in front of the slash were replaced with the corresponding nucleotides or amino acids after the slash.

[c]Specific binding activities were determined for each of the indicated fusion proteins. The concentration of a fusion protein required to give an arbitrary $A_{405}$ the same as that found for wild type B7-DCIg was determined from the linear region of binding curves and expressed as a percentage of specific binding activity of B7-DCIg. Values represent the average of three determinations from each binding curve, and are representative of four experiments.

Residues in mB7-H1 and mB7-DC that significantly reduced or abolished PD-1 when mutated were clustered in equivalent regions of the A'GFCC'C" face of the domains (with one exception in each case), although they often were distant in sequence. In contrast, mutation of conserved residues on the BED face did not reduce binding. Thus, residue conservation on the BED face may be important for other effects such as ligand dimerization or recognition of other proteins.

The PD-1 binding sites mapped to equivalent regions on the opposite A'GFCC'C" face. Mapping of the binding site regions revealed that residues whose mutation negatively (or positively) affected PD-1 binding could form coherent surfaces in both ligands. The proximity of important residues and some residues not important for binding again suggested that the observed effects were specific, and were not a consequence of global structural changes. This was further supported by the ability to produce higher avidity mutants of mB7-H1. Comparison of important residue positions confirmed that the location of the putative binding sites in mB7-H1 and mB7-DC closely corresponded to the CD28/CTLA-4 binding sites in CD86 and CD80.

Surface plasmon resonance analysis of binding of wild type and mutant proteins to PD-1 was largely consistent with the results from the FACS and ELISA analyses. The B7-H1 mutant C113 had a similar or slightly higher maximal response (Rmax) value than the wild type protein (321 resonance units (RU) vs. 291 RU), while the mutant I126 (56.1 RU) showed relatively minimal binding to mPD-1 (FIG. 10A). The wild type B7-DC protein had an Rmax of 227 RU, and the B7-DC mutant K113 did not bind to PD-1 at all (FIG. 10B). These data demonstrated that wild type B7-H1 and mutant C113 had a greater steady state affinity for PD-1 than mutant I126, similar to wild type B7-DC as compared to mutant K113. The B7-H1 mutant C113, wild type B7-H1, and wild type B7-DC all had similar on-rates and off-rates, while only the mutants I126 and K113 showed slower or no on- and off-rates, respectively.

Example 4

Costimulatory Function of B7-H1 and B7-DC Mutants

Figure 11A:
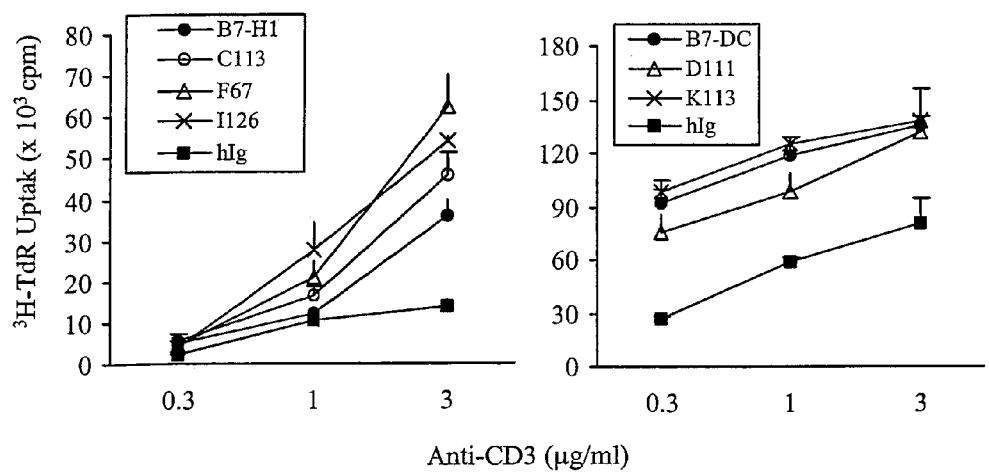
FIGS. 11A and 11B are graphs showing effects of wild type and mutant B7-DC and B7-H1 molecules on T-cell costimulation. Data in FIG. 11A represent T cell proliferation after stimulation with the indicated wild type or mutant B7-H1 and B7-DC Ig fusion proteins in the presence of anti-CD3 mAb coated onto the well-bottoms of 96-well plates at the indicated concentrations. T cell proliferation was measured as incorporation of $^3$H-Thymidine ($^3$H-TdR). Human Ig (hIg) was used as a negative control for the costimulatory molecules. Data depict one representative experiment of three. Data in FIG. 11B represent IFN-γ secretion by T cells cultured in the presence of the indicated Ig fusion proteins and anti-CD3 for 48 or 72 hours. Data depict one representative experiment of three.
Figure 11B:
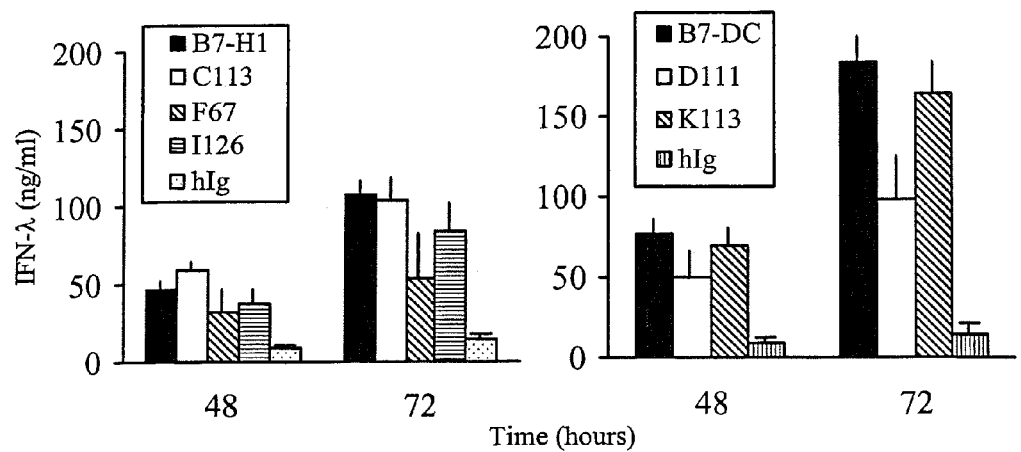

The costimulatory potential of selected mutants also was tested. B7-H1 mutants F67 and I126, and B7-DC mutants K113 and D111 were selected for analysis. Both F67 and I126 had minimal binding to PD-1 in both FACS and ELISA assays (Table 1). Similarly, K113 and D111 did not bind PD-1 (Table 2). As shown in FIGS. 11A and 11B, these mutants were still able to costimulate T cell proliferation and IFN-γ production in comparison with wild type B7-H1 and B7-DC. In fact, B7-H1 mutants F67 and I126 had even slightly increased costimulatory ability as compared to wild type B7-H1. Interestingly, mutant C113, which had approximately 3-fold increased binding capacity to PD-1 as compared to wild type B7-H1 (Table 1), also costimulated T cell proliferation and IFN-γ production. These results indicate that PD-1 is not a costimulatory receptor for B7-H1 and B7-DC.

Figure 12:
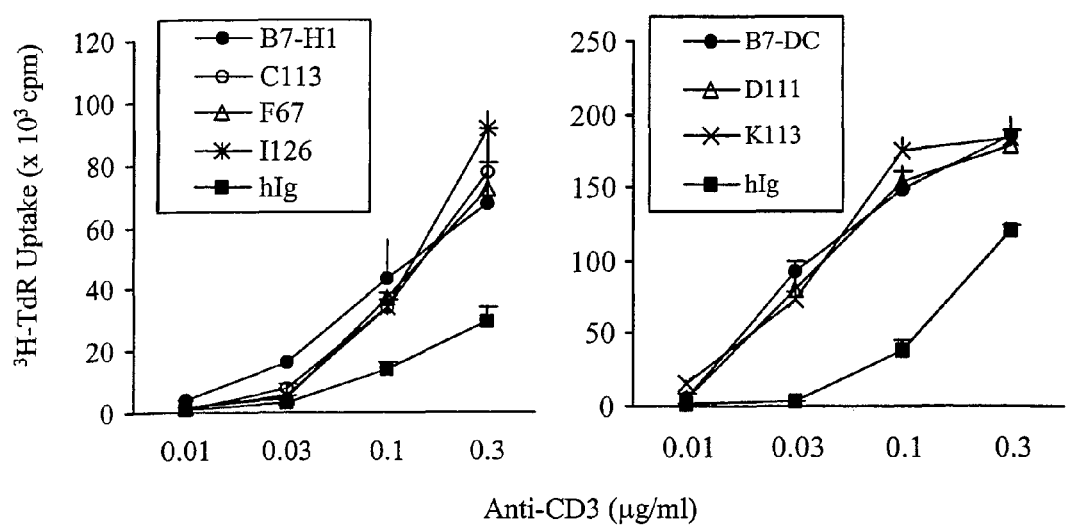
FIG. 12 is a pair of line graphs showing proliferation of PD-1$^{-/-}$ T cells after incubation with the indicated B7-H1 and B7-DC Ig fusion proteins in the presence of anti-CD3 mAb at the indicated concentrations. Human Ig was used as a negative control. Data depict one representative experiment of three.

Although B7-H1 and B-DC might costimulate T cell growth through a yet unknown receptor, these findings could be interpreted as an integrated stimulatory effect of unidentified costimulatory receptor(s) and PD-1. Therefore, the costimulatory effects of these mutants were tested in PD-1 deficient T cells. Wild type and variant B7-H1 polypeptides costimulated proliferation of PD-1$^{-/-}$ T cells as well as or better than PD-1$^{+/+}$ cells (FIG. 12 as compared with FIG. 11A). Similar results were obtained using wild type and variant B7-DC polypeptides. Thus, these observations strongly suggest that B7-H1 and B7-DC costimulate T cell growth through a non-PD-1 receptor.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. An isolated variant B7-DC polypeptide comprising an IgV domain, wherein the variant polypeptide is a variant of wild-type B7-DC polypeptide, has altered binding affinity for PD-1 compared to the wild-type B7-DC polypeptide, and comprises a substitution of an amino acid in the A', B, C, C', C", D, E, F, or G β-strand of wild-type B7-DC polypeptide according to SEQ ID NO:5 or 6.

2. The isolated variant polypeptide of claim 1, which is a variant of murine B7-DC.

3. The isolated variant polypeptide of claim 1, comprising a substitution of the amino acid at position 111 numbered from the initiation methionine of wild-type murine B7-DC (SEQ ID NO:6) or human B7-DC (SEQ ID NO:5).

4. The isolated variant polypeptide of claim 3, wherein said substitution comprises replacing the amino acid at position 111 numbered from the initiation methionine of wild-type murine B7-DC (SEQ ID NO:6) or human B7-DC (SEQ ID NO:5) with a serine residue.

5. The isolated variant polypeptide of claim 1 comprising a substitution of the amino acid at position 113 numbered from the initiation methionine of wild-type murine B7-DC (SEQ ID NO:6) or human B7-DC (SEQ ID NO:5).

6. The isolated variant polypeptide of claim 5, wherein said substitution comprises replacing the amino acid at position 113 numbered from the initiation methionine of wild-type murine B7-DC (SEQ ID NO:6) or human B7-DC (SEQ ID NO:5) with a serine residue.

7. The isolated variant polypeptide of claim 1 comprising a substitution of the amino acid at position 56 numbered from the initiation methionine of wild-type murine B7-DC (SEQ ID NO:6) or human B7-DC (SEQ ID NO:5).

8. The isolated variant polypeptide of claim 7, wherein said substitution comprises replacing the amino acid at position 56 numbered from the initiation methionine of wild-type murine B7-DC (SEQ ID NO:6) or human B7-DC (SEQ ID NO:5) with a serine residue.

9. The isolated variant polypeptide of claim 1, comprising a substitution of the amino acid at position 67 numbered from the initiation methionine of wild-type murine B7-DC (SEQ ID NO:6) or human B7-DC (SEQ ID NO:5).

10. The isolated variant polypeptide of claim 9, wherein said substitution comprises replacing the amino acid at position 67 numbered from the initiation methionine of wild-type murine B7-DC (SEQ ID NO:6) or human B7-DC (SEQ ID NO:5) with a tyrosine residue.

11. The isolated variant polypeptide of claim 1, comprising a substitution of the amino acid at position 71 numbered from the initiation methionine of wild-type murine B7-DC (SEQ ID NO:6) or human B7-DC (SEQ ID NO:5).

12. The isolated variant polypeptide of claim 11, wherein said substitution comprises replacing the amino acid at position 71 numbered from the initiation methionine of wild-type murine B7-DC (SEQ ID NO:6) or human B7-DC (SEQ ID NO:5) with a serine residue.

13. The isolated variant polypeptide of claim 1 comprising a substitution of the amino acid at position 101 numbered from the initiation methionine of wild-type murine B7-DC (SEQ ID NO:6) or human B7-DC (SEQ ID NO:5).

14. The isolated variant polypeptide of claim 13, wherein said substitution comprises replacing the amino acid at position 101 numbered from the initiation methionine of wild-type murine B7-DC (SEQ ID NO:6) or human B7-DC (SEQ ID NO:5) with a serine residue.

15. The isolated variant polypeptide of claim 1 comprising a substitution of the amino acid at position 105 numbered from the initiation methionine of wild-type murine B7-DC (SEQ ID NO:6) or human B7-DC (SEQ ID NO:5).

16. The isolated variant polypeptide of claim 15, wherein said substitution comprises replacing the amino acid at position 105 numbered from the initiation methionine of wild-type murine B7-DC (SEQ ID NO:6) or human B7-DC (SEQ ID NO:5) with an alanine residue.

17. The variant B7-DC polypeptide or fragment thereof of claim 1, wherein the variant B7-DC polypeptide or fragment thereof has decreased binding affinity for PD-1 compared to wild-type B7-DC polypeptide.

18. A fusion polypeptide comprising a first fusion partner comprising the polypeptide of claim 17, and a second fusion partner.

19. The fusion polypeptide of claim 18, wherein the second fusion partner comprises one or more domains of an Ig heavy chain constant region.

20. A method for enhancing an immune response in a mammal comprising administering to the mammal the isolated polypeptide of claim 1 or claim 19, or a nucleic acid molecule encoding the polypeptide.

21. The method of claim 20, wherein the mammal is a human.

22. An isolated polypeptide fragment of murine B7-DC (SEQ ID NO:6) or human B7-DC (SEQ ID NO:5), the polypeptide fragment comprising amino acids 67-71, amino acids 101-105, or amino acids 111-113 of SEQ ID NO:6, wherein the polypeptide inhibits binding of endogenous B7-DC to PD-1.

23. The fragment of claim 22, comprising amino acids 101-113 of murine B7-DC (SEQ ID NO:6) or human B7-DC (SEQ ID NO:5).

24. A method of inhibiting the interaction between PD-1 and B7-DC, the method comprising contacting a PD-1 polypeptide with the polypeptide fragment of claim 22.

25. The method of claim 24, wherein the PD-1 is in vitro.

26. The method of claim 24, wherein the PD-1 is in a mammal.

27. The method of claim 24, wherein the method comprises administering the polypeptide fragment to the mammal.

28. The method of claim 26, wherein the mammal is a human.

29. The isolated polypeptide of claim 1, wherein the B7-DC polypeptide is human B7-DC.

30. The fusion polypeptide of claim 19, wherein the second polypeptide comprises an amino acid sequence corresponding to the hinge, $C_H2$ and $C_H3$ regions of a human immunoglobulin chain.

31. The fusion polypeptide of claim 30, wherein the first polypeptide comprises the extracellular domain of B7-DC or a fragment thereof, and wherein the second polypeptide comprises an amino acid sequence corresponding to the hinge, $C_H2$ and $C_H3$ regions of a human immunoglobulin chain.

32. The isolated variant B7-DC polypeptide of claim 17, wherein the variant B7-DC polypeptide or fragment thereof enhances an immune response in a mammal.

33. The isolated variant B7-DC polypeptide or fragment thereof of claim 1, wherein the variant B7-DC polypeptide or fragment thereof has increased binding affinity for PD-1 compared to wild-type B7-DC polypeptide.

34. The isolated variant B7-DC polypeptide of claim 33, wherein the variant B7-DC polypeptide or fragment thereof enhances an immune response in a mammal.

35. The isolated variant polypeptide of claim 33, which is a variant of murine or human B7-DC.

36. The isolated variant polypeptide of claim 33, comprising a substitution of the amino acid at position 58 number from the initiation methionine of wild-type murine B7-DC (SEQ ID NO:6) or human B7-DC (SEQ ID NO:5).

37. The isolated variant polypeptide of claim 36, wherein the substitution comprises replacing the amino acid at position 58 numbered from the initiation methionine of wild-type murine B7-DC (SEQ ID NO:6) or human B7-DC (SEQ ID NO:5) with a tyrosine residue.

38. An isolated fusion polypeptide comprising a first fusion partner comprising the polypeptide of claim 33, and a second fusion partner.

39. The fusion polypeptide of claim 38, wherein the second fusion partner comprises one or more domains of an Ig heavy chain constant region.

40. The fusion polypeptide of claim 38, wherein the second polypeptide comprises an amino acid sequence corresponding to the hinge, $C_H2$ and $C_H3$ regions of a human immunoglobulin chain.

41. The fusion polypeptide of claim 38, wherein the first polypeptide comprises the extracellular domain of B7-DC or a fragment thereof, and wherein the second polypeptide comprises an amino acid sequence corresponding to the hinge, $C_H2$ and $C_H3$ regions of a human immunoglobulin chain.

42. A fusion polypeptide comprising the IgV domain of B7-DC fused to a second polypeptide, wherein the IgV domain of B7-DC is from human (SEQ ID NO:5) or murine B7-DC (SEQ ID NO:6) and comprises an amino acid substitution relative to wildtype human (SEQ ID NO:5) or murine (SEQ ID NO:6) B7-DC IgV domain, wherein the substitution alters binding affinity for PD-1 compared to the wild-type B7-DC polypeptide.

43. The fusion polypeptide of claim 42, wherein the second polypeptide comprises an amino acid sequence corresponding to the hinge, $C_H2$ and $C_H3$ regions of a human immunoglobulin chain.

44. The fusion polypeptide of claim 42 wherein the amino acid substitution in the extracellular domain occurs at the amino acid residue corresponding to amino acid position 111 numbered from the initiation methionine of wild-type murine B7-DC (SEQ ID NO:6) or human B7-DC (SEQ ID NO:5).

45. The fusion polypeptide of claim 44, wherein the amino acid substitution is with a serine residue.

46. The fusion polypeptide of claim 42, wherein the substitution is at the amino acid residue corresponding to position 113 numbered from the initiation methionine of wild-type murine B7-DC (SEQ ID NO:6) or human B7-DC (SEQ ID NO:5).

47. The fusion polypeptide of claim 46, wherein the substitution is with a serine residue.

48. The fusion polypeptide of claim 42 comprising a substitution of the amino acid is at the amino acid residue corresponding to position 56 numbered from the initiation methionine of wild-type murine B7-DC (SEQ ID NO:6) or human B7-DC (SEQ ID NO:5).

49. The fusion polypeptide of claim 48, wherein the substitution comprises replacing the amino acid corresponding the amino acid at position 56 numbered from the initiation methionine of wild-type murine B7-DC (SEQ ID NO:6) or human B7-DC (SEQ ID NO:5) with a serine residue.

50. The fusion polypeptide of claim 42, comprising a substitution of the amino acid corresponding to the amino acid at position 67 numbered from the initiation methionine of wild-type murine B7-DC (SEQ ID NO:6) or human B7-DC (SEQ ID NO:5).

51. The fusion polypeptide of claim 50, wherein the substitution comprises replacing the amino acid corresponding to the amino acid at position 67 numbered from the initiation methionine of wild-type murine B7-DC (SEQ ID NO:6) or human B7-DC (SEQ ID NO:5) with a tyrosine.

52. The fusion polypeptide of claim 42, comprising a substitution of the amino acid corresponding to the amino acid at position 71 numbered from the initiation methionine of wild-type murine B7-DC (SEQ ID NO:6) or human B7-DC (SEQ ID NO:5).

53. The fusion polypeptide of claim 52, wherein the substitution comprises replacing the amino acid corresponding to the amino acid at position 71 numbered from the initiation methionine of wild-type murine B7-DC (SEQ ID NO:6) or human B7-DC (SEQ ID NO:5) with a serine residue.

54. The fusion polypeptide of claim 42, comprising a substitution of the amino acid corresponding to the amino acid at position 101 numbered from the initiation methionine of wild-type murine B7-DC (SEQ ID NO:6) or human B7-DC (SEQ ID NO:5).

55. The fusion polypeptide of claim 54, wherein the substitution comprises replacing the amino acid corresponding to the amino acid at position 101 numbered from the initiation methionine of wild-type murine B7-DC (SEQ ID NO:6) or human B7-DC (SEQ ID NO:5) with a serine residue.

56. The fusion polypeptide of claim 42, comprising a substitution of the amino acid at position 105 corresponding to the amino acid numbered from the initiation methionine of wild-type murine B7-DC (SEQ ID NO:6) or human B7-DC (SEQ ID NO:5).

57. The fusion polypeptide of claim 56, wherein the substitution comprises replacing the amino acid corresponding to the amino acid at position 105 numbered from the initiation methionine of wild-type murine B7-DC (SEQ ID NO:6) or human B7-DC (SEQ ID NO:5) with an alanine.

\* \* \* \* \*

UNITED STATES PATENT AND TRADEMARK OFFICE
CERTIFICATE OF CORRECTION

PATENT NO.         : 8,039,589 B1
APPLICATION NO.    : 11/932471
DATED              : October 18, 2011
INVENTOR(S)        : Lieping Chen Page 1 of 1

It is certified that error appears in the above-identified patent and that said Letters Patent is hereby corrected as shown below:

Column 42, line 39 (Claim 17), please delete "The variant B7 DC polypeptide or fragment thereof" and insert --The isolated variant polypeptide-- therefor.

Column 42, lines 50-51 (Claim 20), please delete ", or a nucleic acid molecule encoding the polypeptide".

Column 43, line 1 (Claim 27), please delete "claim 24," and insert --claim 26,-- therefor.

Column 43, lines 35-37 (Claim 38), please delete "comprising the polypeptide of claim 33, and a second fusion partner" and insert --and a second fusion partner, said first fusion partner comprising the polypeptide of claim 33-- therefor.

Signed and Sealed this
Seventh Day of February, 2012

David J. Kappos
*Director of the United States Patent and Trademark Office*